US006270959B1

(12) United States Patent
Dekaban et al.

(10) Patent No.: US 6,270,959 B1
(45) Date of Patent: Aug. 7, 2001

(54) HUMAN T-CELL LYMPHOTROPIC VIRUS TYPE II ENVELOPE PROTEIN AND HUMAN MONOCLONAL ANTIBODIES SPECIFIC THEREFOR

(76) Inventors: Gregory A. Dekaban, 14 Gablewood Crescent, London, Ontario (CA), N6G 2Z9; Jacqueline Arp, 345 Grandview Avenue, London, Ontario (CA), N6K 2T1; Steven Kok Hing Foung, 658 Mayfield Ave., Stanford, CA (US) 94305

( * ) Notice: Subject to any disclaimer, the term of this patent is extended or adjusted under 35 U.S.C. 154(b) by 0 days.

(21) Appl. No.: 09/409,025

(22) Filed: Sep. 30, 1999

Related U.S. Application Data

(62) Division of application No. 08/626,452, filed on Apr. 2, 1996, now Pat. No. 5,961,984.

(51) Int. Cl.[7] .................................................. C12Q 1/70
(52) U.S. Cl. .......................... 435/5; 424/208.1; 424/160; 530/412; 530/806
(58) Field of Search ................................ 424/208.1, 160; 435/5; 530/412, 806

(56) References Cited

PUBLICATIONS

Robert–Guroff, M., Nakao, Y., Notake, K. Ito, Y., Sliski, A., and R.C. Gallo. 1982. Natural antibodies to human retrovirus HTLV in a cluster of Japanese patients with adult T cell leukemia. Science. 215:975–978.

Yoshida, M., Seiki, M., Yamaguchi, K., and K. Takasuki. 1984. Monoclonal integration of human T–cell leukemia provirus in all primary tumours of adult T–cell leukemia suggests causative role of human T–cell leukemia virus in the disease. Proc. Natl. Acad. Sci. USA. 81:2534–2537.

Osame, M., Usuku, K., Izumo, S., Ijichi, N., Amitani, H., Igata, A., Matsumoto, M., and M. Tara. 1986. HTLV–I Associated Myelopathy, a new clinical entity. Lancet. 1:1031–1032.

Ijichi, S., Matsuda, T., Maruyama, I., Izumihara, T., Kojima, K., Niimura, T., Maruyama, Y., Sonada, S., Yoshida, A., and M. Osame. 1990. Arthritis in human T lymphotropic virus type (HTLV–I) carrier. Ann. Rheum. Dis. 49:718–721.

Mochizuki, M., Watanabe, T., Yamaguchi, K., Takatsuki, K., Shirao, M., Nakashima, S., Mori, S., Araki, S., and N..Miyata. 1992. HTLV–I uveitis: a distinct clinical entity caused by HTLV–I. Jpn. J. of Cancer Res. 83:236–239.

Lagrenade, L., Hanchard, B., Fletcher, V., Cranston, B., and W. Blattner. 1990. Infective dermatitis of Jamaican children: a marker for HTLV–I infection. Lancet. 336:1345–1347.

De The, G., and R. Bonford. 1993. An HTLV–I vaccine: why, how and for whom? AIDS Res. Hum. Retroviruses. 9:381–386.

(List continued on next page.)

*Primary Examiner*—Hankyel T. Park
(74) *Attorney, Agent, or Firm*—Shoemaker and Mattare, Ltd

(57) ABSTRACT

Isolated and purified envelope protein of HTLV-I is provided devoid of non-envelope protein of HTLV-I and having substantially the same conformation as the envelope protein in native HTLV-I. The protein is produced recombinantly using a dual vaccinia/T7 polymerase system. Non-glycosylated and glycosylated forms of the protein are produced. Glycosylated forms are recognized by antibodies specific for the envelope protein of HTLV-I. Monoclonal antibodies are provided which are specific for the HTLV-I envelope protein and non-binding to HTLV-I envelope protein in denatured form. The HTLV-I envelope protein is cross-reactive with antibodies of HTLV-II and STLV. The envelope protein is useful in diagnosis of infection by HTLV-I and HTLV-II.

10 Claims, 8 Drawing Sheets

OTHER PUBLICATIONS

Lillehoj, E., Tal, C., Nguyen, A., and S. Alexander. 1989. Characterization of env and tax encoded polypeptides of human T–cell leukemia virus type I. Clin. Biotechn. 1:27–41.

De, B., Lairmore, M., Griffis, K., Williams, L., Villinger, F., Quinn, T., Brown, C. Nzilambi, Sugimoto, M., Araki, S., and T. Folks. 1991. Comparative analysis of nucleotide sequences of the partial envelope gene (5' domain) among human T–lymphotropic virus type I (HTLV–I) isolates. Virology. 182:413–419.

Kinoshita, T., Tsujimoto, A., and K. Shimotohno. 1991. Sequence variations in LTR and env regions of HLTV–I do not discriminate between the virus from patients with HTLV–I associated myelopathy and adult t–cell leukemia. Int. J. Cancer. 47:491–495.

Komurian, F., Pelloguin, F., and G. De The. 1991. In vivo genetic variability of human T–cell leukemia virus type I depends more upon geography than upon pathologies. J. Virol. 65:3770–3778.

Pique, C., Tursz, T., and M.–C. Dokhelar. 1990. Mutations introduced along the HTLV–I envelope gene result in a non–functional protein: a basis for envelope conservation EMBO J. 9:4243–4248.

Pique, C., Pham, D., Tursz, T., and M.–C. Dokhelar. 1992. Human T–cell Leukemia Virus Type I envelope protein maturation process: Requirements for syncytium formation. J. Virol. 66:906–913.

Arp, J., Ford, C., Palker, T., King, E., and G. Dekaban. 1993. Expression and immunogenicity of the entire human T–cell leukaemia virus type I envelope protein produced in a baculovirus system. J. Gen. Virol. 74:211–222.

Manca, F., Li Pira, G., Fenoglio, D., Valle, M.T., Kunkl, A., Ferraris, A., Mortara, L., Balderas, R., Arp, J., Baccala, R., Dekaban, G., Dalgleish, A.G., and A.N. Theofilopoulos. 1995. Recognition of HTLV–I envelope protein by human CD4+ T cell lines generated from HTLV–I seronegative individuals. Blood. 85:1547–1554.

Ford, C., Arp, J., King, E., Dekaban, G.A. and T. Palker. 1991. Expression and immunogenicity of HTLV–I envelope proteins by recombinant vaccinia virus, p.253–258. In R.M. Chanock, et al. (eds.), Vaccines 91: Modern Approaches to New Vaccines Cold Spring Harbour Laboratory, New York.

Ford, C.M., Arp, J., Palker, T.J. King, E.E., and G.A. Dekaban. 1992. Characterizatino of the antibody response to three different versions of the HTLV–I envelope protein expressed by recombinant vaccinia viruses: Induction of neutralizing antibody. Virology. 191:448–453.

Ratner, L., Josephs, S., Starcich B., Hahn, B., Shaw, G., Gallo, R. and F. wong–Staal. 1985. Nucleotide sequence analysis of a variant Human T–cell Leukemia Virus (HTLV–Ib) provirus with a deletion in pX–I. J. Virol. 54:781–790.

Elroy–Stein, O., Fuerst, T., and B. Moss. 1989. Cap–independent translation of mRNA conferred by encephalomyocarditis virus 5' sequence improves the performance of the vaccinia virus/bacteriophage T7 hybrid expression system. Proc. Natl. Acad. Sci. USA. 86:6126–6130.

Dales, S., and L. Siminovitch. 1961. The development of vaccinia virus in Earle's L strain cells as examined by electron microscopy, J. Biophys. Biochem. Cytol. 10:475–503.

Mackett, M., Smith, G., and B. Moss. 1984. General method for the production and selection of infectious vaccinia virus recombinants expressing foreign genes. J. Virol. 49:857–864.

Mackett, M., Smith, G., and B. Moss. 1985. The construction and characterization of vaccinia virus recombinants expressing foreign genes, p. 191–211. In D. Rickwood and B.D. Hames (ed.), DNA cloning, vol. 2. IRL Press, Washington D.C.

Fuerst, T., Niles, E., Studier, F., and B. Moss. 1986. Eukaryotic transient–expression system based on recombinant vaccinia virus that synthesizes bacteriophage T7 RNA polymerase. Proc. Natl. Acad. Sci. USA. 83:8122–8126.

Foung, S. and S. Perkins. 1989. Electric field–induced cell fusion and human monoclonal antibodies. J. Immunol. Methods. 116:117–122.

Perkins, S., Zimmermann, U. and S. Foung. 1991. Parameters to enhance hybridoma formation with hypo–osmolar electrofusion. Hum. Antibod. Hybridomas. 2:155–159.

Perkins, S. and S. Foung. 1995. Stabilizing antibody secretino of human Epstein–Barr virus activated B. lymphocytes with hybridoma formatino by electrofusion. In Nickoloff, J. (ed.), Protocols for electroporation and electrofusion of plant and animal cells, in press. Humana Press, New Jersey.

Hayden, D.B., Baker, N.R., Percival, M.P., and P.B. Beckwith. 1986. Modification of the Photosystem II light–harvesting chlorophyll a/b protein complex in maize during chill–induced photoinhibition. Biochim. Biophys. Acta. 851:86–92.

Palker, T., Tanner, M., Scearce, R., Streilein, R., Clark, M. and B. Haynes. 1989. Mapping of immunogenic regions of human T–cell leukemia type I (HTLV–I) gp46 and gp21 envelope glycoproteins with env–encoded synthetic peptides and a monoclonal antibody to gp46. J. Immunol. 142:971–978.

Giri, A., Markham, P., Digilio, L., Hurteau, G., Gallo, R., and G. Franchini. 1994. Isolation of a novel simian T–cell lymphotropic virus from *Pan paniscus* that is distantly related to the human T–cell leukemia/lymphotropic virus types I and II. J. Virol. 68:8392–8395.

Matsushita, S., Robert–Guroff, M., Trepel, J., cossman, J., Mitsuya, H., and S. Broder. 1986. Human monoclonal antibody directed against an envelope glycoprotein of human T–cell leukemia virus type I. Proc. Natl. Acad. Sci. USA. 83:2672–2676.

Hayden, D.B., Baker, N.R., Percival, M.P., and P.B. Beckwith. 1986. Modification of the Photosystem II light–harvesting chlorophyll a/b protein complex in maize during chill–induced photoinhibition. Biochim. Biophys. Acta. 851:86–92.

Trimble, R. and g. Maley. 1984. Optimizing hydrolysis of N–linked high–mannose oligosaccharides by endo–beta–N––acetyl–glucosaminidase H. Analyt. Biochem. 141:515–522.

Plummer, T., Jr., Elder, J., Alexander S., Phelan, A., and A. Tarentino. 1984. Demonstration of peptide: N–glycosidase F activity in endo–beta–N–acetylglucoaminidase F preparations. J. Biol. Chem. 259:10700–10704.

Rowe, J., Perkins, S., Bradshaw, P., Song, G–Y, S. Fuong. 1994. Neutralizing HTLV–human monoclonal antibodies (HMAbs) to conformational epitopes. AIDS Res. Hum. Retroviruses. 10:509.

Lee, T., Coligan, J., Homma, T., McLane, M., Tachibana, N., and M. Essex. 1984. Human T–cell leukemia virus–associated membrane antigens: identity of the major antigens recognized after virus infection. Proc. Natl. Acad. Sci. USA. 81:3856–3860.

Geyer, H., Holschbach, D., Hunsmann, G., and J. Schneider. 1988. Carbohydrates of human immunodeficiency virus: structures of oligosaccharides linked to the envelope glycoproteins 120. J. Biol. Chem. 263:11760–11767.

Goubau, P., Liu, H., DeLange, G. Vandamme, A. and J. Desmyter. 1993. HTLV–II seroprevalence in pygmies across Africa since 1970. AIDS Res. Hum. Retroviruses. 9:709–713.

Komfeld, R., and S. Komfeld. 1985. Assembly of asparagine–linked oligosaccharides. Ann. Rev. Biochem. 54:631–664.

Seiki, M., Hattori, S., Hirayama, Y., and M. Yoshida. 1983. Human adult T–cell leukemia virus: Complete nucleotide sequence of the provirus genome integrated in leukemia cell DNA. Proc. Natl. Acad. Sci. USA. 80:3618–3622.

Chen, Y., Lee, T., Samuel, K., Okayama, A., Tachibana, N., Miyoshi, I., Papas, T., and M. Essex. 1989. Antibody reactivity to different regions of human T–cell leukemia virus type I gp61 in infected people. Journal of Virology 63:4952–4957.

Kiyokawa, T., Yoshikura, H., Hattori, S., Seiki, M., and Yoshida, M. 1984. Envelope proteins of human T–cell leukemia virus: Expression in *Escherichia coli* and its application to studies of env gene functions. Proceeding of the National Academy of Science, U.S.A. 81:6202–6206.

Kuga, T., Hattori, S., Yoshida, M., and T. Taniguchi. 1986. Expression of human t–cell leukemia virus type I envelope protein in *Saccharmyces cerevisiae*. Gene. 44:337–340.

Nyunoya, H., Ogura, T., Kikuchi, M., Iwamoto, H., Yamashita, K., Maekawa, M., Takebe, Y., Miyamura, K., Yamazaki, S., and Shimotohno, K. 1990. Expression of HTLV–I envelope protein of hydrophobic amino–terminal peptide of baculovirus polyhedrin in insect cells and its application for serological assays. AIDS Research and Human Retroviruses. 6:1311–1321.

Samuel, K., Lautenberger, J., Jorcyk, C., Josephs, S., Wong–Staal, F., and T. Papas. 1984. Diagnostic potential for human malignancies of bacterially produced HTLV–I envelope glycoprotein. Science. 226:1094–1097.

Vile, R., Schulz, T., Danos, O., Collins, M., and R. Weiss. 1991. A Murine cell line producing HTLV–I pseudotype virions carrying a selectable marker gene. Virology. 180:420–424.

Sattentau, Q. and J. Moore. 1995. HIV–1 neutralization is determined by epitope exposure on the gp120 oligomer. J. Exp. Med. 182:185–196.

Stamatatos, L. and C. Cheng–Mayer. 1995. Structural modulations of the envelope gp120 glycoprotein of human immunodeficiency virus type 1 upon oligomerization and differential V3 loop epitope exposure of isolates displaying distinct tropism upon virion–soluble receptor binding. J. Virol. 69:6191–6198.

Seiki, M., Hattori, S., Hirayama, Y., and M. Yoshida. 1983. Human adult T–cell leukemia virus: Complete nucleotide sequence of the provirus genome integrated in leukemia cell DNA. Proc. Natl. Acad. Sci. USA. 80:3618–3622.

FIGURE 5

A. Untreated

B. Brefeldin A

C. Tunicamycin

HUMAN T-CELL LYMPHOTROPIC VIRUS TYPE II ENVELOPE PROTEIN AND HUMAN MONOCLONAL ANTIBODIES SPECIFIC THEREFOR

REFERENCE TO RELATED APPLICATION

This application is a divisional of U.S. patent application Ser. No. 08/626,452 filed Apr. 2, 1996 (now U.S. Pat. No. 5,961,984).

FIELD OF INVENTION

The present invention relates to the field of immunology and is particularly concerned with Human T-cell Lymphotropic Virus type I envelope proteins and human monoclonal antibodies specific therefor.

BACKGROUND TO THE INVENTION

Human T-cell Lymphotropic Virus type I (HTLV-I) was the first human retrovirus to be associated with disease, Adult T-cell Leukemia/Lymphoma (ATL; ref. 1, 2—various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure) and later with HTLV-I Associated Myelopathy/Tropical Spastic Paraparesis (HAM/TSP; 3). Recently this virus has been associated with arthropathy (ref. 4), uveitis (ref. 5) and infective dermatitis (ref. 6). HTLV-I has been found in almost every region of the world and it is estimated that approximately 10 to 20 million people are infected (ref. 7).

The envelope protein of HTLV-I is composed of an external surface glycoprotein, gp46 and a noncovalently associated transmembrane anchor protein, gp21; both of these are derived from a common precursor, gp63 (ref. 8). The gp46 HTLV-I envelope protein is one of the smallest retroviral envelope proteins known and exhibits little sequence variability (ref. 9, 10, 11). This genetic stability may be a reflection of the limited coding sequence and a need for structural conservation in order to preserve its functionality. While a number of studies have characterized the HTLV-I gp46 protein (refs. 12, 13), it has been difficult to heterologously express recombinant envelope protein in large amounts for use in biochemical and immunological studies. (refs. 40, 41, 42, 43, 44, 45) We have recently described the expression of the entire HTLV-I envrelope protein, gp63, in a baculovirus expression system (ref. LA). Although the recombinant protein was expressed in the amounts, it was insoluble and the majority of protein was not completely post-translationally processed. Following successful solubilization of this protein, the soluble and insoluble forms of gp63 have been used to generate human T-cells lines in vitro (ref. 15) and high anti-envelope antibody titres in rabbits (ref. 16). Unfortunately, only non-neutralizing antibodies were induced by the recombinant gp63 protein as either insoluble inclusion bodies (ref. 14) or in its soluble form. This baculovirus-expressed envelope protein thus cannot be in the natural conformation that it is present in the virus and thus is not optimal for vaccine or diagnostic purposes.

Our previous study demonstrated that a recombinant vaccinia virus (RVV E3) containing the HTLV-I coding region for gp46 alone, produced the conformationally correct envelope surface protein, induced neutralizing antibodies in mice (refs. 16, 17) and expressed envelope protein at much higher levels that it did when gp21was concomitantly expressed in another construct RVV E1 (ref. 17). In this previous work, however, there was no provision of an isolated and purified envelope protein of Human T-cell Lymphotrophic Virus Type I (HTLV-I) devoid of non-envelope proteins of HTLV-I having substantially the same conformation as the envelope protein in native HTLV-I, especially the Tox and p12$^I$ proteins which have demonstrated oncogenic potential.

It would be advantageous to provide a recombinantly-producted, isolated and purified envelope protein of HTLV-I which is devoid of other HTLV-I proteins and having substantially the same conformation as the native protein in high yields and methods of purification of such proteins. Such proteins have use as antigens, immmunogenic prepared including vaccines, as components of diagnose assays and for the generation of diagnostic reagents. It would also be advantageous to provide human monoclonal antibodies which are HTLV-I envelope protein specific and substantially non-binding to HTLV-I envelope protein in a denatured form.

SUMMARY OF INVENTION

In accordance with one aspect of the present invention, there is provided an isolated and purified envelope protein of Human T-cell Lymphotrophic Virus Type I (HTLV-I) devoid of non-envelope proteins of HTLV-I having substantially the same conformation as the envelope protein in native HTLV-I. This envelope protein is sometimes referred to herein as the "gp46 envelope protein". The envelope protein is provided devoid of non-envelope protein of HTLV-I by production by recombinant means as described in more detail below.

The isolated and purified envelope protein generally is provided in a glycosylated form with an apparent molecular weight of about 47 to about 49 kDa, as determined by sodium dodecyl sulfate gel electrophoresis (SDS-PAGE). The protein provided herein may be in the form of a mixture of two envelope proteins of HTLV-I having an apparent molecular weight of about 47 kDa and about 49 kda respectively.

The isolated and purified envelope protein provided herein generally binds to a HTLV-I envelope protein-specific human monoclonal antibodies which do not bind to denatured envelope protein of HTLV-I, particularly monoclonal antibodies which recognize conformational epitopes of the envelope protein of HTLV-I.

The recombinant procedure described herein produces a mixture of proteins of varying molecular weights and degrees of glycosylation. Accordingly, in another aspect of the invention, there is provided a mixture of at least two isolated and purified envelope proteins of HTLV-I devoid of non-envelope proteins of HTLV-I having an apparent molecular weight which is selected from about 39 kDa, about 43 kDa, about 45 kDa, about 47 kDa and about 49 kDa, as determined by SDS-PAGE, which may include a mixture of all such envelope proteins.

The envelope proteins provided herein are also recognized by antibodies specific for HTLV-II envelope proteins. Accordingly, in another aspect of the present invention, there is provided an isolated and purified envelope protein of HTLV-I devoid of non-envelope proteins of HTLV-I which is recognized by antibodies specific for the envelope protein of Human T-cell Lymphotrophic Virus Type II (HTLV-II).

The present invention also provides an immunogenic composition comprising an immunoeffective amount of an active component, which may be the novel envelope protein provided herein, which may be formulated along with a pharmaceutically acceptable carrier therefor. The immunogenic composition may be formulated as a vaccine for in vivo administration to a host.

The immunogenic composition may be formulated as a microparticle, capsule, ISCOM or liposome preparation. The immunogenic composition may be used in combination with a targeting molecule for delivery to specific cells of the immune system or to mucosal surfaces. Some targeting molecules include strain B12 and fragments of bacterial toxins, as described in WO 92/17167 (Biotech Australia Pty. Ltd.), and monoclonal antibodies, as described in U.S. Pat. No. 5,194,254 (Barber et al). The immunogenic compositions of the invention (including vaccines) may further comprise at least one other immunogenic or immunostimulating material and the immunostimulating material may be at least one adjuvant.

Suitable adjuvants for use in the present invention include, (but are not limited to) aluminum phosphate, aluminum hydroxide, QS21, Quil A, derivatives and components thereof, ISCOM matrix, calcium phosphate, calcium hydroxide, zinc hydroxide, a glycolipid analog, an octadecyl ester of anmino acid, a muramyl dipeptide polyphosphazare, ISCOPRP, DC-chol, DDBA and a lipoprotein and other adjuvants to induce a Th1 response. Advantageous combinations of adjuvants are described in copending U.S. patent application Ser. No. 08/261,194 filed Jun. 16, 1994, assigned to the assignee hereof and the disclosure of which is incorporated herein by reference.

In a further aspect of the invention, there is provided a method of generating an immune response in a host, comprising administering thereto an immuno-effective amount of the immunogenic composition as provided herein. The immune response may be a humoral or a cell-mediated immune response. Hosts in which protection against disease may be conferred include primates including humans.

The present invention additionally provides a method of producing antibodies specific for an envelope protein of HTLV-I, comprising:

(a) administering the envelope protein provided herein to at least one mouse to produce at least one immunized mouse;

(b) removing B-lymphocytes from the at least one immunized mouse;

(c) fusing the B-lymphocytes from the at least one immunized mouse with myeloma cells, thereby producing hybridomas;

(d) cloning the hybridomas;

(e) selecting clones which produce anti-envelope protein antibody;

(f) culturing the anti-envelope protein antibody-producing clones; and then (g) isolating anti-envelope protein antibodies from the cultures.

The present invention further provides a HTLV-I envelope protein specific human monoclonal antibody which is substantially non-binding to HTLV-I envelope protein in a denatured form. Such monoclonal antibody generally binds to the isolated and purified envelope protein which provides the first aspect of this invention.

The monoclonal antibody provided herein preferably recognizes a conformational epitope of the envelope protein of HTLV-I and is capable of neutralizing HTLV-I syncytium formation. Such monoclonal antibody may be one having the characteristics of a monoclonal antibody produced by a hybridoma selected from the group consisting of WA11/1F5, WA07/2F7, WA07/1G7, WA11/2E2, WA11/2F3 and WA04/2B10.

The present invention provides, in an additional aspect thereof, a method for producing an immunogenic composition comprising administering the immunogenic composition provided herein to a first test host to determine an amount and a frequency of administration thereof to elicit a selected immune response against HTLV-I; and formulating the immunogenic composition in a form suitable for administration to a second host in accordance with the determined amount and frequency of administration. The second host may be a human.

The novel envelope protein provided herein is useful in diagnostic procedures and kits for detecting antibodies to retroviruses, including HTLV-I, HTLV-II and related primate T-cell lymphotrophic viruses (PTLVs), such PTLV-L, and STLVs, such as $STLV_{pan-p}$, STLVI, STLVII and other primate retroviruses related to HTLV-II. Further monoclonal antibodies specific for the envelope protein are useful in diagnostic procedure and kits for detecting the presence of HTLV-I protein.

Accordingly, a further aspect of the invention provides a method of determining the presence in a sample, of antibodieS; specifically reactive with an envelope protein of -TTLV-I, HTLV-II or related primate T-cell lymphotrophic viruses PFTLVs), such PTLV-L, and STLVs, such as SLVpanp, STLVI, STLVII and other primate retroviruses related to HTLV-II comprising the steps of:

(a) contacting the sample with the HTLV-I envelope protein or proteins as provided herein to produce complexes comprising the HTLV-I envelope protein and any said antibodies present in the sample specifically reactive therewith; and (b) determining production of the complexes.

In a further aspect of the invention, there is provided a method of determining the presence, in a sample, of an envelope protein of HTLV-I,comprising the steps of:

(a) immunizing a host with HTLV-I envelope protein as provided herein, to produce antibodies specific for the envelope protein;

(b) contacting the sample with the antibodies to produce complexes comprising any envelope protein present in the sample and said envelope protein specific antibodies; and (c) determining production of the complexes.

A further aspect of the invention provides a diagnostic kit for determining the presence of antibodies in a sample specifically reactive with an envelope protein of HTLV-I, HTLV-II or related primate T-cell lymphotrophic viruses (PTLVs), such PTLV-L, and STLVS, such as $STLV_{pan-p}$, STLVI, STLVII and other primate retroviruses related to HTLV-II, comprising:

(a) the envelope protein as provided herein;

(b) means for contacting the envelope protein with the sample to produce complexes comprising the envelope protein and any said antibodies present in the sample; and (c) means for determining production of the complexes.

The invention also provides a diagnostic kit for detecting the presence, in a sample, of an envelope protein of HTLV-I, comprising:

(a) an antibody specific for the novel envelope protein as provided herein;

(b) means for contacting the antibody with the sample to produce a complex comprising the envelope protein and envelope protein-specific antibody; and (c) means for determining production of the complex.

In this application, the term "HTLV-I envelope protein" is used to define a family of HTLV-I envelope proteins generally having an apparent molecular weight of from about 39 to about 49 kDa and includes proteins having variations in their amino acid sequences. In this application, a first protein is a "functional analog" of a second protein if the first protein is immunologically related to and/or has the same function as the second protein. The functional analog may be, for example, a fragment of the protein or a substitution, addition or deletion mutant thereof. The invention also extends to such functional analogs.

Advantages of the present invention include:

an isolated and purified envelope protein of HTLV-I produced recombinantly to be devoid of non-envelope proteins of HTLV-I and having substantially the same conformation as the envelope protein in native HTLV-I;

HTLV-I envelope protein specific human monoclonal antibodies which are substantially non-binding to HTLV-I envelope protein in non-denatured form; and a diagnostic kits and immunological reagents for specific identification of hosts infected by HTLV-I, HTLV-II and related primate T-cell lymophotrophic viruses.

BRIEF DESCRIPTION OF DRAWINGS

The present invention will be further understood from the following detailed description and Examples with reference to the accompanying drawings in which:

FIG. 5 shows the expression of HTLV-I envelope protein in Human H9 versus HeLa cells. Immuno blot analysis of H9 and HeLa cell lysates ($2.0 \times 10^5$ cells) co-infected with vTME-46/vTF7-3 at an moi of 4. The blot was incubated with HAM/TSP sera;

GENERAL DESCRIPTION OF INVENTION

Figure 1:
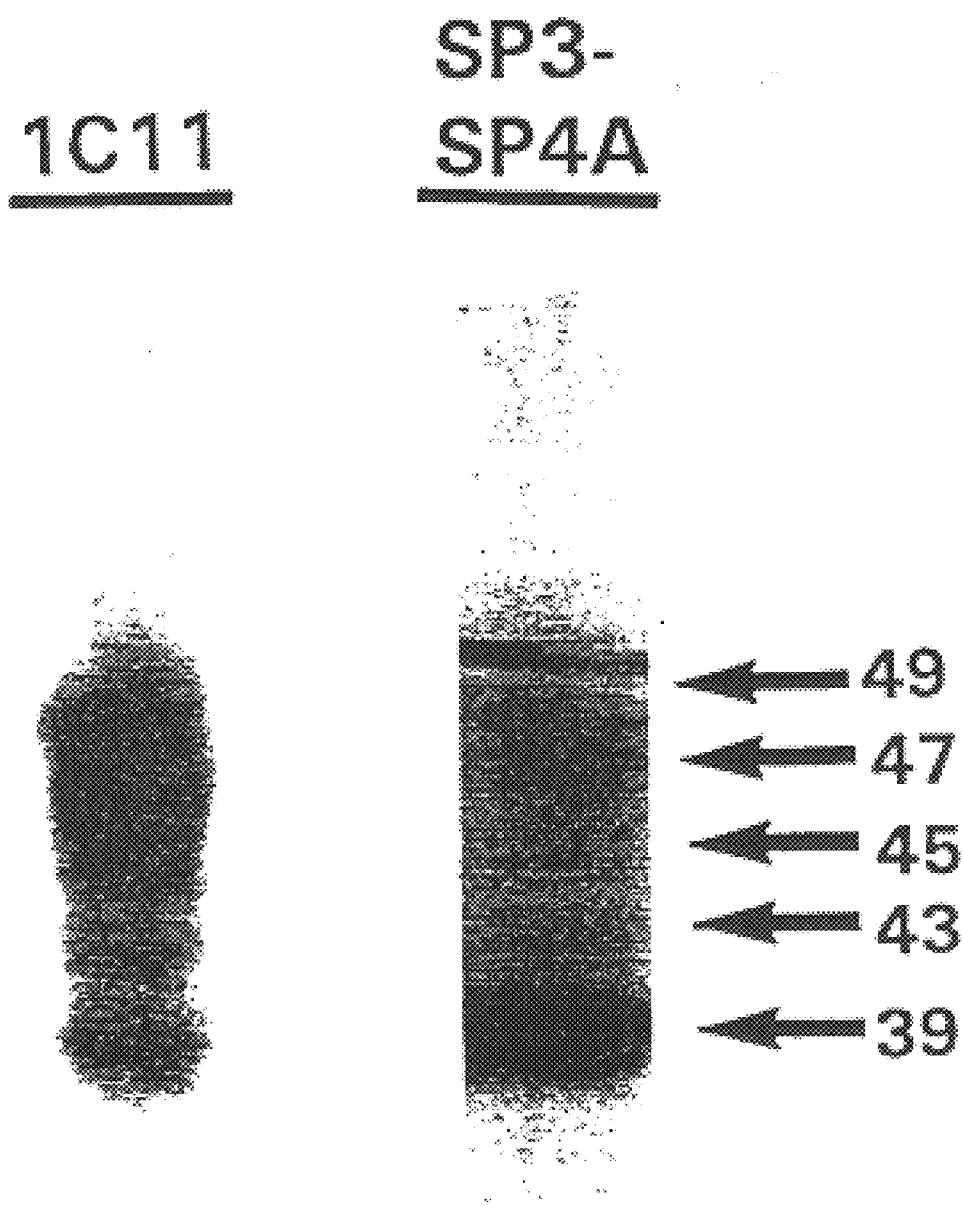
FIG. 1 shows an immunoblot analysis of HTLV-I envelope proteins produced in HeLa cells. The primary antibody used: 1C11, anti-gp46 mouse Mab; SP3/SP4A, anti-envelope peptide rabbit polyclonal sera.

As described above, the present invention provides certain novel HTLV-I envelope proteins which are provided devoid of non-envelope proteins of HTLV-I and with substantially the same conformation as the envelope protein in native HTLV-I. This novel protein may be prepared using recombinant procedures, wherein the protein is expressed from a suitable expression vector and then isolated and purified.

In one specific embodiment of the invention, a vaccinia/T7 polymerase system was used to express the recombinant HTLV-I surface envelope protein in mammalian cells. This strategy required the construction of a recombinant vaccinia virus, vTME-46, encoding the HTLV-I gp46 gene fragment under the control of the T7 bacteriophage promoter and terminator regulatory elements. Co-infection with a second recombinant virus, vTF7-3, encoding the T7 polymerase gene (ref. 23) resulted in expression of the gp46 envelope protein.

Five differentially glycosylated forms of the surface envelope protein were produced by vTME-46/vTF7-3-infected HeLa cells, having an apparent molecular weight of about 39 kDa, about 43 kDa, about 45 kDa, about 47 kDa and about 49 kDa. N-glycosylation inhibition by tunicamycin and N-glycan removal with endo H and PNGase F revealed that the 39 kDa protein was the unglycosylated form and the 49 kDa protein was the fully glycosylated envelope protein. Each oligosaccharide on average contributes approximately 2 kDa to the apparent molecular mass of the protein (ref. 38); thus the observed 10 kDa ladder of different recombinant envelope forms was consistent with differential attachment of four oligosaccharides. This result indicated that all four potential N-glycosylation sites in gp46 (ref. 39) were utilized for oligosaccharide modification in the vaccinia/T7 polymerase system.

The envelope glycoproteins expressed by the mammalian system appeared to have both mannose-rich and hybrid oligosaccharides attached, as determined by endo H digestion. The glycosylation of the recombinant envelope proteins resembled that of gp46 produced by HUT-102-HTLV-I infected human cells, which were also sensitive to endo H digestion (ref. 35).

The dual infection system (vTME-46/vTF7-3) was compared with the single vaccinia virus recombinant system (RVV E3) in which expression of gp46 was under control of the vaccinia promoter P7.5. The efficiency of the T7 polymerase/T7 promoter-dependent expression by the dual vaccinia system was apparent in its ability to express more total HTLV-I surface envelope protein with faster kinetics and less extensive cytopathic destruction of the host cells. The promoter of such enhanced quantities of expression product and the availability of the HTLV-I envelope protein specific human monoclonal antibodies described herein enables, for the first time, the isolation and purification of HTLV-I envelope protein having substantially the same conformation as the envelope protein in HTLV-I.

Optimal conditions for the vTME-46/vTF7-3 dual expression system were determined to attain maximal HTLV-I envelope production. Best yields of the recombinant envelope protein were observed approximately 36 to 48 hours following dual infection. There was no advantage in allowing the infection to progress further due to the increased cytopathic effects and cell death mediated by vaccinia virus. When the effect of virus multiplicities was studied in the dual gp46 expression system, it appeared that a multiplicity of about two pfu/cell yielded maximal amounts of glycosylated envelope protein. Higher multiplicities of infection of 4,7 and 10 did not result in increased yields of the recombinant protein. The requirement of low viral multiplicities in the system employed herein is in contrast to what was observed in a dual vaccinia system constructed to express beta-galactosidase (ref. 14), which required viral multiplicities of ten for maximal yields.

Having regard to the observation that recombinant protein expression levels can vary between different cell types, human H9 T-cells were compared to human HeLa epithelial cells as hosts for dual vaccinia infection and recombinant envelope protein expression. While H9 and HeLa cells are very different in function and origin, the apparent size of the glycosylated (49 and 47 kDa) and unglycosylated (39 kDa) envelope protein forms produced by the two cell types did not vary significantly. This result suggested that similar post-translational processing of the recombinant envelope protein occurs in different cell types of endothelial (HeLa) and lymphocytic (H9) origin. In terms of protein yields, however, there was a marked difference between the two cell lines. The vTME-46/vTF7-3-infected HeLa cells produced 4-fold more envelope protein than the same number of co-infected H9 cells by densitometer analysis.

Native folding of the recombinant HTLV-I envelope proteins produced by the dual vaccinia system was shown by their ability to bind several HTLV-I envelope-specific human monoclonal antibodies. All HTLV-I-specific antibodies tested were capable of neutralizing HTLV-I syncvtium formation. These human monoclonal antibodies do not recognize linear epitopes of denatured HTLV-P envelope protein am shown by their lack of binding to viral lysate-based Western blots. Instead, the monoclonal antibodies appear to bind to discontinuous, conformational epitopes as determined by radioimmunoprecipitation and immunofluorescence of HTLV-I infected cell lines (ref. 44). The ability of these conformation-dependent monoclonal antibodies to bind to the recombinant HTLV-I envelope proteins produced in the dual vaccinia system, indicates that the proteins are being folded and maintained in a native conformation. The most glycosylated recombinant envelope protein forms (49 and 47 kDa) appear to be processed and folded substantially in the manner of the envelope protein expressed by HTLV-I infected human cells, since the recombinant proteins were readily immunoprecipitated with the full panel of conformation-dependent human monoclonal antibodies as well as several polyclonal sera obtained from HTLV-I-infected human patients.

Conformational integrity of recombinant envelope protein was also indicated by the ability of the specific human monoclonal antibodies WA07/1G7, WA07/2F7 and WA11/2F3 to bind to dual vaccinia-infected HeLa cells as detected by indirect immunofluorescence. The WA07/1G7 and WAO7/2F7 monoclonal antibodies exhibited the most avid neutralizing/syncytium inhibition properties of the six monoclonal antibodies tested, inhibiting greater than 90% of syncytium formation at concentrations less than 5 $\mu$g IgG$_1$/ml. Strong binding of these two monoclonal antibodies to the recombinant HTLV-I envelope protein suggested that the protein contains conformational epitopes that are significant in virus neutralization/synctium inhibition.

The absence or weak immunofluorescence exhibited by the other human monoclonal antibodies may be due to their weaker affinity for the native HTLV-I envelope protein as suggested by the higher concenstraous of their antibodies required to sustain 90% syncytium inhibition of HTLV-I infected cells (23 to 90 $\mu$g IgG$_1$/ml). Weak immunofluorescence demonstrated by some of the monoclonal antibodies may also be the result of slight sequence variation between the HTLV-I envelope sequence encoded by the recombinant vaccinia virus and that of the viral strain of the monoclonal antibody hybridoma source. Significant differences in epitope topography due to sequence variation of the two envelope proteins are unlikely since all six monoclonal antibodies appeared to be equally capable of immunoprecipitating the recombinant envelope proteins at an IgG$_1$ concentration of 7.5 $\mu$g/ml-below the 100% syncytium inhibition threshold of all six monoclonal antibodies. More likely, the lack of antibody binding during immunofluorescence analysis may result from the expression of gp46 in the absence of gp21 by the dual vaccinia system. Without this transmembrane anchor protein, the orientation of the recombinant gp46 (rgp46) on the membrane surface of vTME-46/vTF7-3 infected cells may not be identical to native gp46 found on the membrane of HTLV-I-infected cells. If the HTLV-I envelope protein naturally exists as an oligomer on the surface of virions and infected cells, it may be expected that the gp46 oligomeric complex has differentially exposed epitopes compared to a monomeric form. Distinct differences in the conformation and accessibility of various epitopes of HIV gp120 monomers and oligomers has been detected using domain-specific monoclonal antibodies (refs. 46, 47). The unavailability of specific epitopes would prevent the binding of particular antibodies to surface-associated rgp46; however, these epitopes would become available once the recombinant envelope proteins were in solution, as demonstrated by their immunoprecipitation by all six human monoclonal antibodies.

The biochemical and conformational integrity of the recombinant envelope proteins produced in the dual vaccinia system suggests that they may prove to be an effective vaccine candidate. The conserved epitopes recognized by HTLV-I, HTLV-II and STLV$_{pan-p}$ sera suggest that the recombinant envelope proteins may afford protection against infection of various HTLV-I isolates, independent of viral primary sequence and potentially confer cross-protection against HTLV-II and related primate T-cell lymphotrophic viruses (PTLVs), such PTLV-L, and STLVs, such as STLV$_{pan-p}$, STLVI, STLVII and other primate retroviruses related to HTLV-II.

Preferential precipitation of the most glycosylated recombinant HTLV-I envelope forms (47 and 49 kDa) by the various polyclonal human sera and the conformational-dependent human monoclonal antibodies indicates that proper glycosylation of the recombinant is important in establishing the native conformation of the protein. However, an optimal vaccine against HTLV-I may require inclusion of all five differentially glycosylated forms of the recombinant envelope protein since each form may present different epitopes to the immune system.

The recombinant HTLV-I envelope proteins provided herein and produced recombinantly as described herein are also useful diagnostic reagents in light of the fact that they were recognized by various HTLV-II-infected human sera and serum from a Pan paniscus chimpanzee infected with STLV$_{pan-p}$ (ref. 29). The STLV$_{pan-p}$ did not react with either HTLV-I gp46 viral antigen, HTLV-I envelope peptide MTA-1, or HTLV-II peptide K55 found on HTLV-I 2.3 blot strips. In addition, the envelope sequence could not be amplified by PCR from this infected monkey cell DNA by HTLV-I/STLV-I envelope-specific primers (ref. 29). The observation that the recombinant HTLV-I envelope proteins provided herein and produced in the vaccinia/T7 polymerase system, are recognized and immunoprecipitated by sera from the distantly related STLV$_{pan-p}$, indicates that these proteins are useful in diagnosis of HTLV-I and HTLV-II in human Pygmy tribes (Bambuti and Bakola) who demonstrate an atypical HTLV-I and HTLV-II seropositivity (refs. 36, 37). This diagnostic embodiment is particularly useful to screen primates for human or simian related retroviruses where organs are to be used in xenotransplantation. In particular, HTLV-I ELISA kits use envelope antigen deficient in glycoproteins. The envelope glycoprotein of HTLV-I having eventually the same conformation as the envelope protein in native HTLV-I allows for the ability to recognize and detect conformational sensitive antibodies.

Accordingly, the HTLV-I gp46 envelope protein has been expressed in a vaccinia/T7 polymerase system. The protein was produced at high levels in a properly processed and folded form. Glycosylation of the recombinant gp46 in this mammalian system occurs at all four potential N-linked glycosylation sites and resembles that produced by an HTLV-I infected cell. The biochemical and structural homology with native gp46 suggests that the recombinant envelope protein might be useful as a vaccine in eliciting protective immune responses in vivo, and possibly aid in identifying the cell surface receptor utilized by HTLV-I during infection. In addition, this protein may prove to be an instrumental diagnostic reagent for the identification of novel human retroviruses.

It is clearly apparent to one skilled in the art, that the various embodiments of the present invention have many applications in the fields of vaccination, diagnosis, treatment of viral infections and the generation of immunological reagents. A further non-limiting discussion of such uses is further presented below.

1. Vaccine Preparation and Use

Immunogenic compositions, suitable to be used as vaccines, may be prepared from the envelope protein of HTLV-I, as well as analogs and fragments thereof, as disclosed herein. The immunogenic composition elicits an immune response which produces antibodies, including anti-envelope protein antibodies and antibodies that are opsonizing or virus neutralizing.

Immunogenic compositions, including vaccines, may be prepared as injectables, as liquid solutions or emulsions. The envelope protein of HTLV-I may be mixed with pharmaceutically acceptable excipients which are compatible therewith. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions can take the form of solutions, suspensions, tablets, pills, capsules, sustained release formulations or powders and contain about 1 to 95% of the HTLV-I envelope protein. The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the lactoferrin receptor protein. Suitable regimes for initial administration and booster doses are also variable, but may include an initial administration followed by subsequent administrations. The dosage may also depend on the route of administration and will vary according to the size of the host.

The concentration of the HTLV-I envelope protein in an immunogenic composition according to the invention is in general about 1 to 95%. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunogenicity can be significantly improved if the antigens are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and a HBsAg vaccine has been adjuvanted with alum. While the usefulness of alum is well established for some applications, it has limitations. For example, alum is ineffective for influenza vaccination and inconsistently elicits a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant bacterial products, slot as muramyl dipeptide (MDP) and lipopolysaccharice as well as lipid A, and lipid.

To efficiently induce humoral immune responses (HIR) and cell-mediated immunity (CMI), immunogens are often emulsified in adjuvants. Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:

(1) lack of toxicity;
(2) ability to stimulate a long-lasting immune response;
(3) simplicity of manufacture and stability in long-term storage;
(4) ability to elicit both CMI and HIR to antigens administered by various routes, if required;
(5) synergy with other adjuvants;
(6) capability of selectively interacting with populations of antigen presenting cells (APC);
(7) ability to specifically elicit appropriate $T_H1$ or $T_H2$ cell-specific immune responses; and
(8) ability to selectively increase appropriate antibody isotype levels (for example, IgA) against antigens.

U.S. Pat. No. 4,855,283 granted to Lockhoff et al on Aug. 8, 1989 which is incorporated herein by reference thereto teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. (U.S. Pat. No. 4,855,283 and ref. 29) reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, incorporated herein by reference thereto, teaches that octadecyl tyrosine hydrochloride (OTH) functioned as an adjuvant when complexed with tetanus toxoid and formalin inactivated type I, II and III poliomyelitis virus vaccine. Also, Nixon-George et al. (ref. 30), reported that octadecyl esters of aromatic amino acids complexed with a recombinant hepatitis B surface antigen, enhanced the host immune responses against hepatitis B virus.

Lipidation of synthetic peptides has also been used to increase their immunogenicity. Thus, Wiesmuller 1989, describes a peptide with a sequence homologous to a foot-and-mouth disease viral protein coupled to an adjuvant tripalmityl-s-glyceryl-cysteinylserylserine, being a synthetic analogous of the N-terminal part of the lipoprotein from Gram negative bacteria. Furthermore, Deres et al. 1989, reported in vivo priming of virus-specific cytotoxic T lymphocytes with synthetic lipopeptide vaccine which comprised of modified synthetic peptides derived from influenza virus nucleoprotein by linkage to a lipopeptide, N-palmityl-s-[2,3-bis(palmitylxy)-(2RS)-propyl-[R]-cysteine (TPC).

2. Immunoassays

The envelope protein HTLV-I of the present invention is useful as an immunogen for the generation of anti-envelope protein antibodies, as an antigen in immunoassays including enzyme-linked immunosorbent assays (ELISA), RIAs and other non-enzyme linked antibody binding assays or procedures known in the art for the detection of antibodies. In ELISA assays, the envelope protein is immobilized onto a selected surface, for example, a surface capable of binding proteins such as the wells of a polystyrene microtiter plate. After washing to remove incompletely adsorbed envelope protein, a nonspecific protein, such as a solution of bovine serum albumin (BSA) that is known to be antigenically neutral with regard to the test sample, may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from about 2 to 4 hours, at temperatures such as of the order of about 25° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound envelope protein of HTLV-I, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a colour development upon incubating with an appropriate chromogenic substrate. Quantification may then be achieved by measuring the degree of colour generation using, for example, a visible spectra spectrophotometer.

The envelope protein of HTLV-I provided herein also recognizes antibodies to HTLV-II and other T-cell lymphotroptic retroviruses, such as $STLV_{pan-p}$, STLVI, STLVII and other primate retroviruses related to HTLV-II and hence is useful for detection of monoclonal antibodies specific to such diseases in suitable biological samples.

Biological Deposits

Certain hybridomas produce human monoclonal antibodies specific for HTLV-I envelope protein that according to aspects of the present invention that are described and referred to herein have been deposited with the American Type Culture Collection (ATCC) located at 12301 Parklawn Drive, Rockville, Md., USA, 20852, pursuant to the Budapest Treaty and prior to the filing of this application. Samples of the deposited hybridomas will become available to the public upon grant of a patent based upon this United States patent application. The invention described and claimed herein is not to be limited in scope by the hybridomas deposited, since the deposited embodiment is intended only as an illustration of the invention. Any equivalent or similar hybridomas that produce similar or equivalent antibodies as described in this application are within the scope of the invention.

Deposit Summary

| Hybridomas | ATCC Designation | Date Deposited |
| --- | --- | --- |
| WA07/1G7 | | |
| WA07/2F7 | | |
| WA11/2F3 | | |
| WA11/1F5 | | |
| WA04/2B10 | | |

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, and immunology used but not explicitly described in this disclosure and these Examples are amply reported in the scientific literature and are well within the ability of those skilled in the art.

Example 1

This Example describes the construction of a recombinant plasmid containing the gene encoding the HTLV-I gp46 protein.

The HTLV-I envelope gene fragment encoding gp46 was derived from the plasmid pMT-2 (provided by Dr. R. C. Gallo, NCI/NIH; ref. 18). Two translational stop codons were placed immediately downstream of the gp46 coding region by insertion of a KpnI-EcoRI oligonucleotide. Plasmid pTME-46 was constructed by insertion of the 945 base pair (bp) envelope fragment (NcoI-XmaI) into the expression vector, pTM-1, proviced by Dr. B. Moss (NIH, NIAID, LVD; ref. 19).

Example 2

This Example describes the construction of recombinant vaccinia virus.

Mouse thymidine kinase negative ($TK^-$) L cells and human HeLa cells (American Type Tissue Culture Collection) were grown in Dulbecco modified Eagle medium containing 10% fetal bovine serum (FBS; gibco-BRL) and 100 units/ml of penicillin G and streptomycin The recombinant expression vector, pTME-46, was used as the vehicle for insertion of the HTLV-I envelope glycoprotein gp46 gene fragment into the vaccinia virus genome (strain J, provided by Dr. S. Dales, University of Western Ontario; Ref. 20). The recombinant vaccinia transfer vector (pTME-46) was constructed by inserting the HTLV-I envelope gp46 gene fragment immediately downstream of the bacteriophage T7 promoter of pTM-1 (ref. 19). The presence of the encephalomyocarditis virus (EMC)5' untranslated region between the T7 promoter and the gp46 gene promised efficient translation of the uncapped envelope RNA (ref. 19).

Recombinant virus was prepared by infecting mouse $TK^-L$ cells with wild-type vaccinia virus and transfecting them with calcium phosphate-precipitated pTME-46 plasmid DNA (refs. 21, 22). The cells were harvested and $TK^-$ vaccinia virus was isolated by three successive plaque assays on $TK^-$ cells in the presence of 5-bromodeoxyuridine (BUdR) 25 $\mu$g/ml. Following southern blot confirmation, large stocks of recombinant virus (vTME-46) were prepared under nonselective conditions in HeLa cells. The recombinant vaccinia virus expressing T7 RNA polymerase, vTF7-3, was obtained from Dr. T. Fuerst and Dr. B. Moss (through the AIDS Research and Reference Reagent Program of AIDS, NIAID, HIH; ref. 23). The single recombinant vaccinia virus RVV E3 was used as a positive control and has been previously described in detail (refs. 16, 17). RVV E3 contains the identical gp46 gene fragment as vTME-46, but expression is regulated by the vaccinia early/late promoter P7.5.

Example 3

This Example describes the analysis of recombinantly produced gp46.

The isolated vTME-46 viral clone was capable of T7 promoter-controlled expression of HTLV-I gp46 upon co-infection with the vaccina virus vTF7-3 (ref. 23), which encodes the highly efficient bacteriophage T7 polymerase. Western blot analysis of dually infected HeLa cells revealed expression of five forms of the surface envelope protein, ranging in molecular weight from about 39 to about 49 kDa. Their HTLV-I envelope origin was shown by their specific immunoreactivity to both anti-gp46 1C11 monoclonal antibody and polyclonal anti-SP3/SP4A envelope peptide sera (FIG. 1).

For immunoblotting, cell pellets were resuspended in extraction buffer and 1 mM PMSF. Following addition of an equal volume of 2× Laemmli buffer, the samples were boiled for 10 minutes and briefly sonicated. The supernatants were electrophoresed and transferred from a SDS/6M urea 12% polyacrylamide gel (ref. 29) to Immobilon P membrane (Millipore). Blots were blocked in a solution of 5% skim milk powder (ref. 30) at room temperature for 5 hours. Blots were incubated in the appropriate primary antibody, diluted in blocking buffer, overnight at 4° C. with rocking. Primary antibodies include (i) 1C11, an anti-gp46 mouse monoclonal antibody (ref. 28); (ii) anti-SP3/4A rabbit polyclonal serum (SP3 and SP4A peptide sequences were derived from gp46; (ref. 28); (iii) human HTLV-I patient sera (HAM/TSP); (iv) human HTLV-II patient sera (American Red Cross); (v) human "HTLV-indeterminate" patient sera (Canadian Red Cross); and (vi) polyclonal serum from a pygmy chimpanzee (Pan paniscus) infected with STLVpan-p; (ref. 29). Blots were then washed in blocking buffer and exposed to goat anti-mouse, goat anti-rabbit or goat anti-human IgG antibodies (Abs) conjugated to alkaline phosphatase or horse radish peroxidase (Jackson ImmunoResearch Laboratories Inc.) at a final dilution of 1:5000, for 30 minutes at room temperature. The blot were washed and exposed to substrate according to the manufacturer's instruction (Blot Detection Kit for the alkaline phosphatase conjugated 2° Abs or Enhanced Chemiluminescence for the. horse radish conjugated 2° Abs; Amersham International, PLC).

To determine if the five variant forms of the surface envelope protein resulted from differential glycosylation of the protein, vTME-46/vTF7-3 infected cell lysates were digested with endoglycosidase H (endo H) and glycopeptidase F (PNGase F).

Culture supernatants were supplemented with 1 mM ethylenediaminetetraacetic acid (EDTA) and 1 mM phenyl-methyl-sulfonyl-fluoride. Cells were lysed in cold extraction buffer (pH 7.6: 100 mM NaCl, 10 mM sodium phosphate, 1% Triton X-100, 0.5% sodium deoxycholate, 0.1% SDS, 1 mM EDTA, and 1 mM PMSF). Supernatants and cell lysates were pre-cleared for 18 hours at 4° C. by incubation with 60 μl Protein G Plus/A Agarose (Oncogene Science), which had been preincubated for 2 hour at 4° C. with normal sera of the appropriate species. The Protein G Plus/A Agarose was pelleted and the resulting supernatant was divided into $5 \times 10^6$ cell equivalents. Immunoprecipitations were performed at 4° C. for 18 hours, in the presence of 40 μl of Protein G Plus/A agarose and various HTLV-I specific antisera as specified. Anti-gp46 mouse monoclonal antibody 1C11 was provided by Dr. Tom Palker (Duke University, North Carolina; ref. 28) as tissue culture supernatant and diluted 1:4. HTLV-I envelope-specific human monoclonal antibodies (HMAbs; WA11/1F5; WA07/2F7; WA07/1G7; WA11/2E2; WA11/2F3; and WA04/2B10) were added at a concentrated of 7.5 μg of IgG/ml of suspension. Polyclonal human sera from HAM/TSP patients were used at dilutions of 1:4,000 to 1:20,000, as specified. Human sera from an HTLV-II positive individual was used at a dilution of 1:400. Polyclonal sera from a pygmy chimpanzee (Pan paniscus) infected with STLVpan-p was provided by Dr. G. Franchini (NCI, Maryland) and was solved 1,200. Immune complexes were washed 4 times with extractioin buffer and then, resuspended in the appropriate buffer.

For radiolabelling cells were labelled with [$^{35}$S]L-cysteine (0.125 mCi/$5 \times 10^6$ cells; NEN) for 5 hours in cysteine-free media appropriate for the cell-type utilized, supplemented with 2% dialyzed FBS. When appropriate, 2 μg/ml of tunicamycin was added to the washing and incubated media.

Following immunoprecipitation with mouse monoclonal antibody 1C11, immune complexes were washed four times in extraction buffer. Protein equivalents of $2.5 \times 10^6$ cells were then digested with endoglycosidase H (endo H) or glycopeptidase F (PNGase F) at 37° C. for 20 hours. EndoH digestion was performed in the presence of 25 mM sodium acetate, pH 5.0, 1 mM PMSF and 12 mU endoH (Boehringer Mannheim). For PNGase F digestion, the immune complexes were incubated 25 mM sodium phosphate, pH 7.0, 1% Nonidet P-40, 1 mM EDTA, 1 mM PMSF and 1.5U of PNGase F (Boehringer Mannheim). Digestion products were compared to immunoprecipitates obtained from vTME-46/vTF7-3 infected cells treated with 2 μg/ml tunicamycin for 8 hours prior to radiolabelling.

The endo H enzyme is only able to remove glycan branches of mannose-rich or hybrid glycoproteins but not those of complex glycoproteins (ref. 32) while PNGase F will remove all N-linked oligosaccharides independent of complexity (ref. 33). Digestion products were compared to immunoprecipitates obtained from vTME-46/vTF7-3 infected cells treated with the N-glycosylation inhibitor, tunicamycin.

Figure 2:
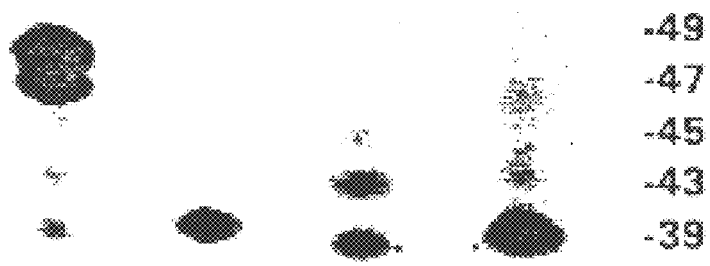
FIG. 2 shows the N-glycosylation of recombinant HTLV-I envelope protein forms. Lysates of $2.5 \times 10^6$ [$^{35}$S]-cysteine-labelled cells were immunoprecipitated with mouse monoclonal antibody 1C11 and digested with endo H or PNGase F. Untr., immunoprecipitate of untreated vTME-46/vTF7-3 infected cell lysate; EndoH and PNGF, immunoprecipitates of untreated vTME-46/vTF7-3 infected cell lysate digested with endonuclease H and PNGase F respectively; Tunc., immunoprecipitate of tunicamycin-treated dual vaccinia infection lysate.

As shown in FIG. 2, immunoprecipitation of normal infected cell lysates with anti-gp46 monoclonal antibody 1C11 yielded the five variant forms of the surface envelope protein, 39-49 kDa. Complete Endo H digestion of the normal infected cell lysates produced only the 39 kDa protein form. Digestion with PNGase F repeatedly produced both the 43 and 39 kDa forms. Resistance of the 43 kDa protein form to PNGase F digestion suggests that one glycosylation site may be located in a region of the protein that is not readily susceptible/accessible to PNGase F. As expected, dual infection in the presence of tunicamycin yielded only the 39 kDa protein from upon radioimmunoprecipitation. No protein forms of molecular weight less than 39 kDa were visualized suggesting that the 39 kDa form represents the completely unglycosylated envelope protein. The 10 kDa shift in molecular mass observed following endoglycosidase digestion or tunicamycin treatment is consistent with the loss of four oligosaccharrides and suggested that all four potential N-linked glycosylation sites of the recombinant envelope protein are utilized for glycan addition (ref. 48). The envelope glycoproteins expressed by this mammalian system have both mannose-rich and hybrid oligosaccharides attached, as determined by endo H digestion.

Samples were resuspended in an equal volume of 2x Laemmli sample buffer, boiled for 10 minutes and analyzed by SDS-PAGE using 12% polyacrylamide SDS/6M urea gels.

Example 4

This Example describes the optimization of expression of HTLV-I envelope proteins.

Figure 3:
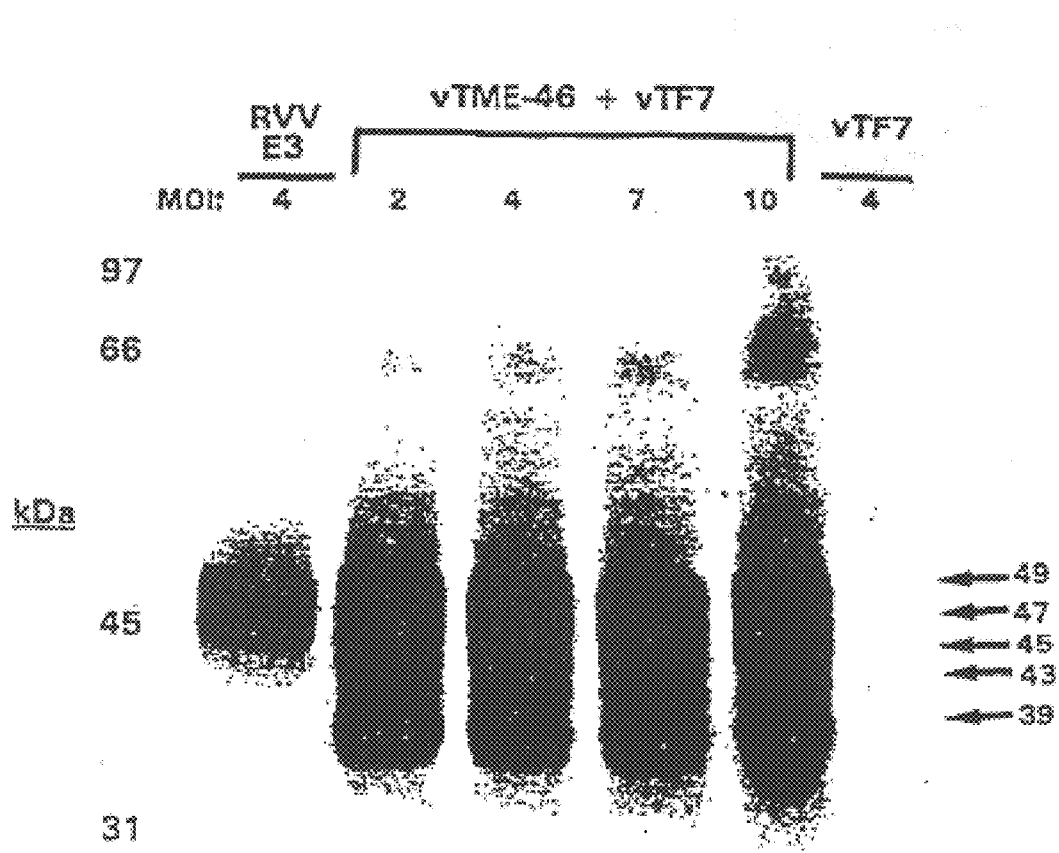
FIG. 3 shows the effect of multiplicity of infection upon envelope protein production by immunoblot analysis HeLa cells ($2.0 \times 10^5$ cells) infected with both vTM-46/vTF7-3, RVV E3 alone or vTF7-3 alone, at various virus multiplicities. HAM/TSP sera was used for immunoblot detection.

Since the T7 RNA polymerase and the HTLV-I gp46 envelope genes are carried on different viruses, we determined the amount of each virus needed for optimal expression. HeLa cells were co-infected with recombinant viruses vTF7-3 and vTME-46 at a range of multiplicities of infection. Upon western blot analysis, it appeared that a multiplicity of 2 pfu/cell appeared to yield maximal amounts of glycosylated envelope protein (FIG. 3). Higher mois of 4, 7 and 10 pfu/cell did not result in increased yields of the recombinant protein forms.

The dual infection system (vTME-46/vTF7-3) was compared with a single vaccinia virus recombinant system (RVV E3) in which expression of gp46 was under control of the vaccinia promoter P7.5. This vaccinia promote-rP7.5, controlling gp46 expression in RVV E3, was the same as that regulating expression of the T7 polymerase gene in recombinant virus vTF7-3. The high efficiency of T7 polymerase/ T7 promoter-dependent expression was observed when vTME-46/vTF7-3 infection at a moi of 2 (FIG. 3, lane 2) expressed twice as much total envelope protein (total of all the variously glycosylated forms) as compared by densitometry to that produced by single vaccinia RVV E3 infection at a moi of 4 pfu/cell (FIG. 3, lane 1).

Figure 4:
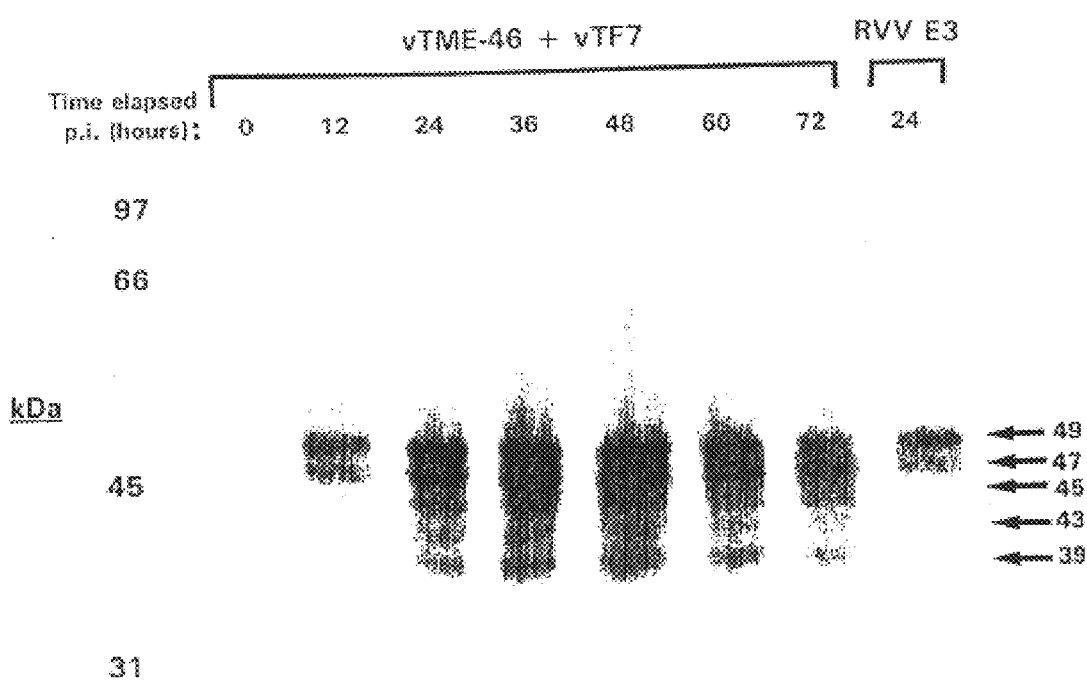
FIG. 4 shows a time course of HTLV-I envelope protein production by immunoblot analysis of cell lysates ($1.2 \times 10^5$ cells) infected with recombinant vaccinia at an MOI of 2 and harvested at the designated times. The blot was incubated with HAM/TSP sera.

To further determine the conditions for optimal expression, a time course of HTLV-I envelope expression in infected HeLa cells was examined. Cells dually infected with vTME-46/vTF7-3 or singly infected with RVW E3 were harvested at various times and the proteins were analyzed by immunoblotting with sera from an HTLV-I infected patient (FIG. 4). Maximal yields of the HTLV-I surface envelope forms by the dual vaccinia/T7 polymerase system appear to occur between 36 and 48 hours post infection (p.i.). Already at 12 hours p.i., the vTME-46/ vTF7-3 infection was capable of producing more total HTLV-I envelope protein than the single vaccinia system, RVV E3, was able to produce at 24 hours post-infection.

Human H9 T-cells were compared to human HeLa epithelial cells as hosts for dual vaccinia virus infection and recombinant envelope protein expression. Both cell lines were infected with the same viral stocks, at the same multiplicities and harvested at the same time. Each infection was examined by both western blot analysis and immunofluorescence for envelope protein expression.

Figure 5:
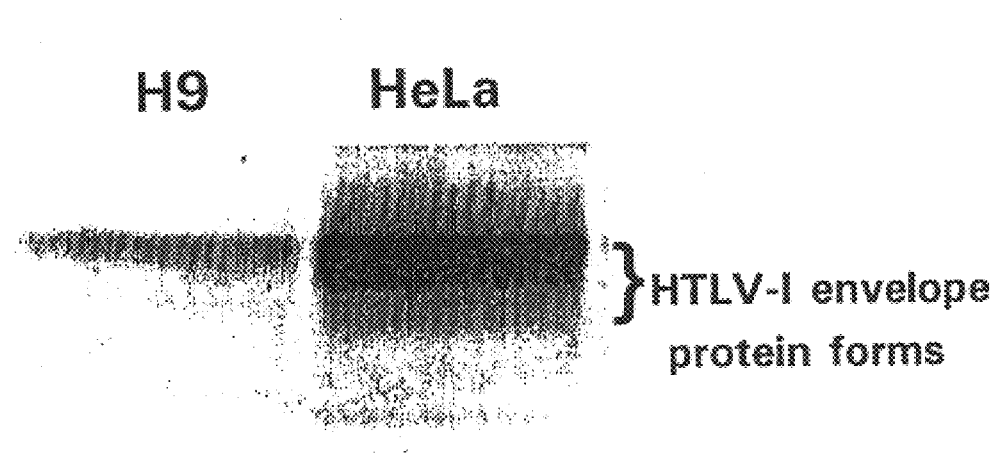

Western blot analysis revealed that HeLa cells produced 4-fold more envelope protein than the same number of H9 cells (FIG. 5). The five different envelope forms (39–49 kDa) are seen upon dual vaccinia infection of HeLa cells (FIG. 5, lane 2) while infected H9 cells express only the two most glycosylated envelope forms, 47 kDa and 49 kDa (FIG. 5, lane 1) and trace amounts of the 39 kDa protein. The difference in expression levels was also apparent upon immunofluorescence analysis of the two infected cell lines. Strong immunofluorescence of >90% of the HeLa cells in the monolayer was observed, in contrast to moderate immunofluorescence of only 30% of the H9 cells. Higher virus multiplicities of 8 and 10 pfu/cell did not appear to increase the amount of gp46 expression by H9 cells or the percentage of vaccinia-infected cells. Single infections with vTME-46 suggested that this recombinant virus is restricted in its infectivity of H9 cells, but not of HeLa cells.

For indirect immunofluorescence of dual recombinant vaccinia-infected cells, human H9 T-cells were infected at a multiplicity of infection (moi) of 4 for 1 hour at room temperature. The free viral inoculum was removed and the infection was allowed to progress for 24 hours. The cells were washed three times in phosphate buffered saline (PBS) containing 2% FBS and resuspended at a final concentration of 8×10⁶ cells/ml. Each spot of a 24-spot teflon-coated super-cured slide (HTC) received 3 μl of cell suspension. HeLa cells were infected in suspension at an moi of 4 for 1 hour at room temperature. The viral supernatant was removed and the cells were resuspended at a final concentration of 1.6×10⁵ cells/ml. Three hundred μl of cells suspension was plated per well in permanox 6-chamber slides (Nunc) and incubated for 24 hours. Following air-drying, all slides were fixed in room temperature acetone for 10 minutes. Uninfected cells and those cells infected with only one recombinant virus, vTF7-3, were included on each slide as negative controls slides were rinsed twice in PBS (pH 7.2) supplemented with 2% FCS. Non-specific binding was blocked by incubating the washed cells in a 4% solution of skim milk powder in PBS (Blotto) for 1 hour at room temperature. Cells were further incubated 30 minutes at 37° C. in 1:20 dilutions of various primary sera (i) HTLV-I envelope-specific human monoclonal antibodies at 40 μg/ml (WA11/1F5; WA07/2F7; WA07/1G7; WA11/2E2; WA11/ 2F3; and WA04/2B10;44); (ii) Human monoclonal antibody 0.5-alpha specific for gp46 (ref. 30); (iii) human HTLV-I-infected patient sera (HAM/TSP). After washing, cells were incubated for 30 minutes at 37° C. with goat anti-human IgG fluorescein isothiocyanate conjugated antibody (GAH-FITC, Jackson ImmunoResearch) diluted in blocking solution. Rinsed cells were viewed on an Olympus BH-2 fluorescence microscope with a fluorescein filter.

Example 5

This Example illustrates that epitopes of HTLV-I gp46 is shared with HTLV-II and $STLV_{pan-p}$.

Figure 6:
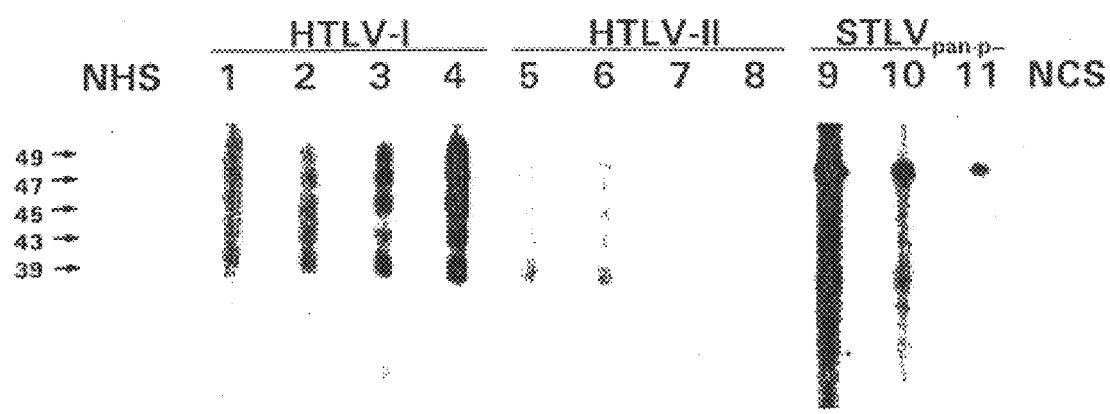
FIG. 6 shows reactivity of HTLV-I, HTLV-II and $STLV_{pan-p}$ sera with HTLV-I envelope protein. HeLa cell lysates infected with vTME-46/vTF7-3 were immunoblotted with normal human serum (NHS 1:500 dilution); asymptomatic HTLV-I-infected patient sera (lanes 1 and 2, patients A and B @ 1:500); sera from HTLV-I infected patients diagnosed with HAM/TSP (lane 3, patient C @ 1:10000; lane 4, patient D @1:4000); HTLV-II-infected patient sera (lane 5–8, patient E–H @1:500 dilution); $STLV_{pan-p}$-infected pygmy chimp serum (lane 9, 1:100; lane 10, 1:200; lane 11, 1:400 dilution); normal pygmy chimpanzee serum (NCS, 1:100 dilution)
Figure 7:
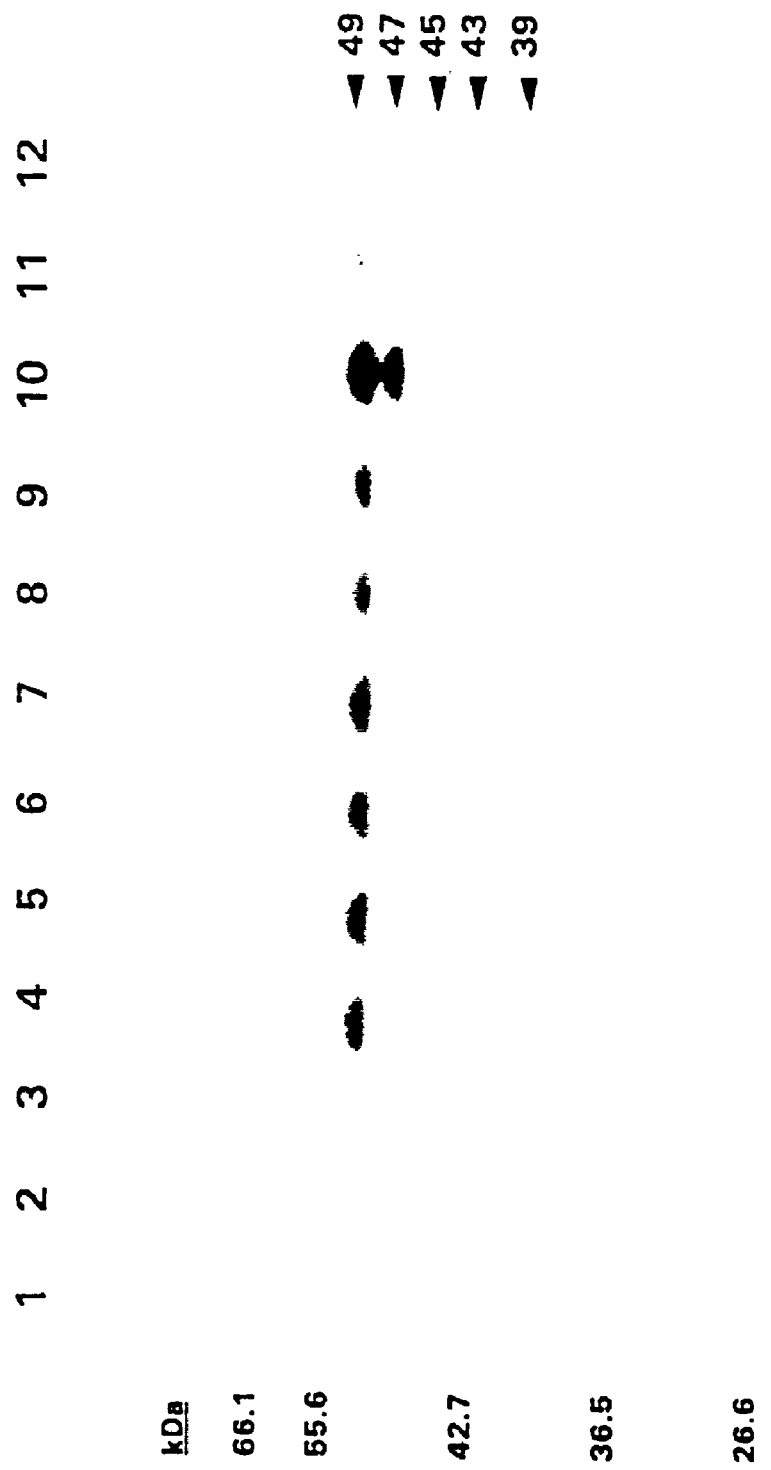
FIG. 7 shows the radioimmunoprecipitatin of vaccinia-infected cell lysates with HTLV-I envelope-specific human monoclonal antibodies. [$^{35}$S]-cysteine-labelled proteins from vTME-46/vTF7-3 infected HeLa cells (lanes 3–10) were immunoprecipitated with equal IgG concentrations (7.5 μg/ml] of HTLV-I-specific human monoclonal antibodies (lane 4, WA11/1F5; lane 5, WA07/2F7; lane 6, WA07/G7; lane 7, WA11/2E2; lane 8, WA11/2F3; and lane 9, WA04/2B10); or an anti-CMV isotype-matched human monoclonal antibody (lane 3, 7.5 μg IgG/ml RO4); or polyclonal sera from HTLV-I infected patients diagnoses with HAM/TSP (lane 10, patient C @ 1:20000; lanes 11 and 12, patients D and I @ 1:4000). Radiolabelled lysates from singly vTF7-3-infected HeLa cells were not immunoprecipitated with polyclonal HTLV-I infected patient C serum (lane 1 @ 1:4000) or human monoclonal antibody, WA04/2B10 (lane 2, 7.5 μg/IgG/ml), were negative controls.
Figure 8:
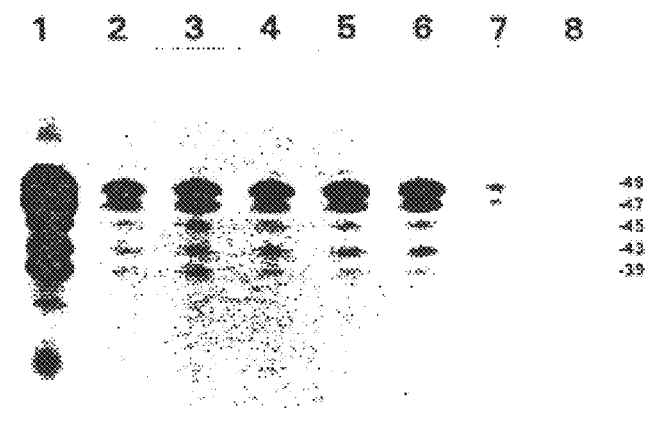
FIG. 8 shows recombinant envelope proteins were expressed by vTME-46/vTF7-3 infected HeLa cells in the absence or presence of the glycosylation inhibitors Brefeldin A and tunicamycin. Equivalent amounts of [$^{35}$S]-cysteine-labelled lysates (vTME-46/vTF7-3 infections: panel A, untreated; panel B, Brefeldin A-treated; panel C, tunicamycin-treated) were immunoprecipitated with the same series of polyclonal sera and monoclonal antibodies. Lane 1, 1C11 mAb; lane 2, HAM/TSP patient C @ 1:20000; lane 3, HAM/TSP patient D @ 1:4000; lane 4, WA11/1F5 [7.5 μg/ml]; lane 5, WA07/1G7 [7.5 μg/ml]; lane 6, WA07/2F7 [7.5 μg/ml]; lane 7, HTLV-II infected human sera @ 1:400; lane 8, $STLV_{pan-p}$ infected chimp sera @ 1:200.
Figure 8:
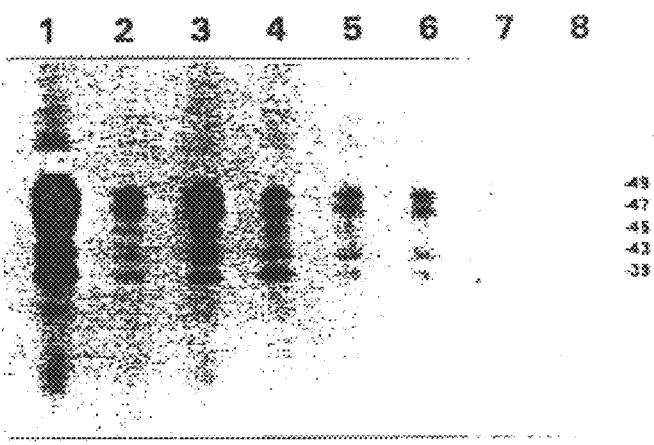
Figure 8:
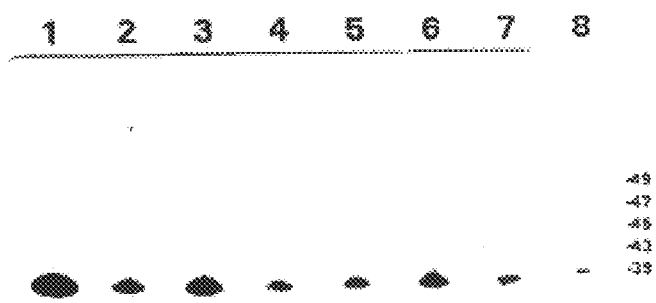

A panel of HTLV-I positive sera (confirmed by ELISA and PCR) from both asymptomatic and HAM/TSP patients was screened for reactivity to the recombinant envelope proteins produced in the vTME-46/vTF7-3 infected HeLa cell system (FIG. 6, lane 1–4). Despite different clinical status, all HTLV-I positive sera recognized each of the five glycosylated recombinant envelope proteins upon western blot analysis. FIG. 6 contains a representative panel of asymptomatic HTLV-I patient sera (lanes 1 and 2) and HAM/TSP patient sera (lanes 3 and 4).

Western blot reactivity of HTLV-II sera with the recombinant envelope proteins produced by the dual vaccinia/T7 polymerase system was also tested. All HTLV-II positive samples tested had been previously confirmed by ELISA and PCR to be,HTLV-I negative/HTLV-II positive by the American Red Cross. Upon western blotting, all 11 samples of HTLV-II-infected patient serum tested recognized one or more of the recombinant HTLV-I envelope protein forms. Seroreactivity to the 47 kDa envelope protein was consistently observed in all the HTLV-II positive samples. FIG. 6 contains a panel of four representative HTLV-II human sera which demonstrated heterologous reactivity patterns to the various envelope forms (lanes 5–8). Some HTLV-II individuals exhibited seroreactivity patterns identical to sera from individuals infected with HTLV-I (FIG. 6, compare lanes 5 and 6 to lanes 1 to 4).

Eight additional sera were obtained from the Canadian Red Cross that had been previously identified as "HTLV-indeterminate" by analysis with the diagnostic Biotechnology HTLV Blot 2.3 strips. Interestingly, all eight "indeterminate" serum samples (100%) exhibited western blot reactivity to one or more of the recombinant HTLV-I protein forms produced by the dual vaccinia/T7 polymerase system. Binding to the 47 kDa protein was observed in 7/8 cases (data not shown). Thus, the recombinant envelope proteins allowed identification of HTLV infected individuals that was not previously possible. No reactivity to any HTLV-I envelope proteins was observed in the normal human serum samples tested thus far (example FIG. 6).

When sera from a pygmy chimp infected with a novel $STLV_{pan-p}$ strain (ref. 29) was screened by western blot, predominant reactivity was observed to the fully glycosylated 49 kDa protein and the unglycosylated 39 kDa HTLV-I envelope proteins (FIG. 6, lanes 1 to 11). Low level reactivity of the $STLV_{pan-p}$ sera to the intermediate glycosylated forms was observed following longer film exposures of the blot. In addition to recognition of the recombinant proteins in a denatured form, the sera from the $STLV_{pan-p}$ inferred chimpanzee and HTVL-I infected and HTLV-II infected humans were also capable of their immunoprecipitation. The two most glycosylated forms the envelope protein (47 and 49 kDa) were preferentially bound and precipitated by all the clinical samples tested. Dr. Giri and colleagues reported that the $STLV_{pan-p}$ did not react with either HTLV-I gp46 viral antigen, HTLV-I envelope peptide MTA-1, or HTLV-II peptide K55 found on HTLV-I 2.3 blot strips (Cellular Products). In addition, envelope sequence could not be amplified by PCR from this infected monkey cell DNA by HTLV-I/STLV-I envelope-specific primers (ref. 29). The recombinant HTLV-I envelope proteins, produced here are recognized and immunoprecipitated by sera form the distantly related $STLV_{pan-p}$, and these proteins may also be useful in diagnosis of HTLV-I and HTLV-II infection in human Pygmy tribes (Bambuti and Bakola) who demonstrate an atypical HTLV-I and HTLV-II seropositivity (refs. 36, 37) as well as to other more distantly related human retroviruses.

Example 6

This Example describes the generation of human monoclonal antibodies specific for HTLV-I gp46.

B lymphocytes from a HAM/TSP patient were isolated, activated with Epstein-Barr virus (EBV), and fused to mouse-human heteromyeloma cell lines by electrofusion, as previously described (refs. 24, 25, 26). Briefly, B cell enriched populations were prepared by rosetting out T cells with 2-aminoethylsiothioronium bromide hydrobromide treated sheep red blood cells. B lymphocytes were activated a $10^4$ cells/well with 10–305 v/v supernatant from the B95-8 marmoset line as a source of EBV, and when proliferating and yellowing the supernatant, were screened for IgG anti-HTLV-I activity by indirect immunofluorescence assay with MT-2 cells fixed on a slide (ref. 27). Hybridomas were produced by fusing cells from reactive wells to heteromyeloma fusion partners by electrofusion using an alternating current of 1 MHz 6V AC, and then screened for initial activity in the same manner as the EBV activated B cells, cloned to stabilize and ensure monoclonality, and supernatant produced for the further characterization. The WA07 hybrids were produced fusing $1.5 \times 10^6$ EBV activated B cells to $K_6H_6$-B5 (courtesy of R Levy, Stanford University) in iso-osmolar fusion medium 300L3) with 3 pulses of 15 microseconds at 1.75 kV/cm DC. WA4 2B10 was produced fusing $1.5 \times 10^5$ EBV activated B cells to H73C11 in hypoosmolar fusion medium (100OL3) with 1 pulse of 10 seconds at 1.25 kV/cm DC.

This procedure produced human monoclonal antibodies specific for the HTLV-I envelope protein, designated WA11/1F5, WA07/2F7, WA07/1G7, WA11/2E2, WA11/2F3 and WA04/2B10 and the characteristics of these are shown in Table I below.

TABLE I

B cells from a HAM/TSP patient were EBV activated and fused by electrofusion with mouse-human heteromycloma cells. Specific HMAbs were identified and characterized by immunofluorescence assay (IFA) with fixed cells or with live cell assays (LCA) with HTLV-I or HTLV-II infected cells, by Western blots, by RIPA and by syncytium inhibition assays (SIA)

| ANTIBODY | IFA I | IFA II | LCA I | LCA II | WESTERN BLOT | RIPA | SIA |
|---|---|---|---|---|---|---|---|
| WA07/1G7 | + | + | + | + | 0 | gp68 | ++ |
| WA07/2F7 | + | + | + | + | 0 | gp68 | ++ |
| WA07/2F9 | + | + | + | + | 0 | gp68 | + |
| WA11/2F3 | + | +/− | + | +/− | 0 | gp68 | + |
| WA11/2E2 | + | +/− | + | +/− | 0 | gp68 | |

TABLE I-continued

B cells from a HAM/TSP patient were EBV activated and fused by electrofusion with mouse-human heteromycloma cells. Specific HMAbs were identified and characterized by immunofluorescence assay (IFA) with fixed cells or with live cell assays (LCA) with HTLV-I or HTLV-II infected cells, by Western blots, by RIPA and by syncytium inhibition assays (SIA)

| ANTIBODY | IFA I | IFA II | LCA I | LCA II | WESTERN BLOT | RIPA | SIA |
|---|---|---|---|---|---|---|---|
| WA11/1F5 | + | 0 | + | +/− | 0 | gp68 | + |
| WA04/2B10 | + | 0 | + | 0 | 0 | gp68 | ++ |
| WA07/2B10 | + | 0 | + | 0 | gp46 | gp68 | 0 |
| WA08/2E9 | + | 0 | + | 0 | 0 | 0 | 0 |
| WA07/1E4 | + | + | 0 | 0 | gp21; p21E | 0 | 0 |
| WA11/2C2 | + | 0 | 0 | 0 | 0 | | 0 |

The data collectively indicates HTLV-I HMAbs to the transmembrane protein, one nonconformational and three conformational epitopes of the envelope protein.

SUMMARY OF THE DISCLOSURE

In summary of this disclosure, the present invention provides novel isolated and purified envelope protein of Human T-cell Lymphotrophic Virus Type I (HTLV-I) devoid of non-envelope proteins of HTLV-I having substantially the same conformation as the envelope protein in native HTLV-I and methods or purification of such envelope proteins. Also provided are human monoclonal antibodies specific for conformational epitopes of the HTLV-I envelope protein which are substantially non-binding to HTLV-I envelope protein in a denatured form. Modifications are possible within the scope of the invention. REFERENCES 1. Robert-Guroff, M., Nakao, Y., Notake, K. Ito, Y., Sliski, A., and R. C. Gallo. 1982. Natural antibodies to human retrovirus HTLV in a cluster of Japanese patients with adult T cell leukemia. Science. 215:975–978.
2. Yoshida, M., Seiki, M., Yamaguchi, K., and K. Takatsuki. 1984. Monocloral integration of human T-cell leukemia provirus in all primary tumours of adult T-cell leukemia suggests causative role of human T-cell leukemia virus in the disease. Proc. Natl. Acad. Sci. USA. 81:2534–2537.
3. Osame, M., Usuku, K., Izumo, S., Ijichi, N., Amitani, H., Igata, A., Matsumoto, M., and M. Tara. 1986. HTLV-I Associated Myelopathy, a new clinical entity. Lancet. 1:1031–1032.
4. Ijichi, S., Matsuda, T., Maruyama, I., Izumihara, T., Kojima, K., Niimura, T., Maruyama, Y., Sonoda, S., Yoshida, A., and M. Osame. 1990. Arthritis in human T lymphotropic virus type (HTLV-I) carrier. Ann. Rheum. Dis. 49:718–721.
5. Mochizuki, M., Watanabe, T., Yamaguchi, K., Takatsuki, K., Shirao, M., Nakashima, S., Mori, S., Araki, S., and N. Miyata. 1992. HTLV-I uveitis: a distinct clinical entity caused by HTLV-I. Jpn. J. of Cancer Res. 83:236–239.
6. Lagrenade, L., Hanchard, B., Fletcher, V., Cranston, B., and W. Blattner. 1990. Infective dermatitis of Jamaican children: a marker for HTLV-I infection. Lancet. 336:1345–1347.
7. De The, G., and R. Bonford. 1993. An HTLV-I vaccine: why, how and for whom? AIDS Res. Hum. Retroviruses. 9:381–386.
8. Lillehoj, E., Tal, C., Nguyen, A., and S. Alexander. 1989. Characterization of env and tax encoded polypeptides of human T-cell leukemia virus type I. Clin. Biotechn. 1:27–41.
9. De, B., Lairmore, M., Griffis, K., Williams, L., Villinger, F., Quinn, T., Brown, C., Nzilambi, Sugimoto, M., Araki, 9. S., and T. Folks. 1991. Comparative analysis of nucleotide sequences of the partial envelope gene (5' domain) among human T-lymphotropic virus type I (HTLV-I) isolates. Virology. 182:413–419.
10. Kinoshita, T., Tsujimoto, A., and K. Shimotohno. 1991. Sequence variations in LTR and env regions of HTLV-I do not discriminate between the virus from patients with HTLV-I associated myelopathy and adult t-cell leukemia. Int. J. Cancer. 47:491–495.
11. Komurian, F., Pelloguin, F., and G. De The. 1991. In vivo genetic variability of human T-cell leukemia virus type I depends more upon geography than upon pathologies. U. Virol. 65:3770–3778.
12. Pique, C., Tursz, T., and M. -C. Dokhelar. 1990. Mutations introduced along the HTLV-I envelope gene result in a non-functional protein: a basis for envelope conservatino? EMBO J. 9:4243–4248.
13. Pique, C., Pham, D., Tursz, T., and M. -C. Dokhelar. 1992. Human T-cell Leukemia Virus Type I envelope protein maturation process: Requirements for syncytium formation. J. Virol. 66:906–913.
14. Arp, J., Ford, C., Palker, T., King, E., and G. Dekaban. 1993. Expression and immunogenicity of the entire human T-cell leukaemia virus type I envelope protein produced in a baculovirus system. J. Gen. Virol. 74:211–222.
15. Manca, F., Li Pira, G., Fenoglio, D., Valle, M. T., Kunkl, A., Ferraris, A., Mortara, L., Balderas, R., Arp, J., Baccala, R., Dekaban, G., Dalgleish, A. G., and A. N. Theofilopoulos. 1995. Recognition of HTLV-I envelope protein by human CD4+ T cell lines generated from HTLV-I seronegative individuals. Blood. 85:1547–1554.
16. Ford, C., Arp, J., King, E., Dekaban, G. A. and T. Palker. 1991. Expression and immunogenicity of HTLV-I envelope proteins by recombinant vaccinia virus, p.253–258. In R. M. Chanock, et al. (eds.), Vaccines 91: Modern Approaches to New Vaccines Cold Spring Harbour Laboratory, New York.
17. Ford, C. M., Arp, J., Palker, T. J. King, E. E., and G. A. Dekaban. 1992. Characterizatino of the antibody response to three different versions of the HTLV-I envelope protein expressed by recombinant vaccinia viruses: Induction of neutralizing antibody. Virology. 191:448–453.
18. Ratner, L., Josephs, S., Starcich B., Hahn, B., Shaw, G., Gallo, R. and F. wong-Staal. 1985. Nucleotide sequence analysis of a variant Human T-cell Leukemia Virus (HTLV-Ib) provirus with a deletion in pX-I. J. Virol. 54:781–790.
19. Elroy-Stein, O., Fuerst, T., and B. Moss. 1989. Cap-independent translation of mRNA conferred by encephalomyocarditis virus 5' sequence improves the performance of the vaccinia virus/bacteriophage T7 hybrid expression system. Proc. Natl. Acad. Sci. USA. 86:6126–6130.
20. Dales, S., and L. Siminovitch. 1961. The development of vaccinia virus in Earle's L strain cells as examined by electron microscopy, J. Biophys. Biochem. Cytol. 10:475–503.
21. Mackett, M., Smith, G., and B. Moss. 1984. General method for the production and selection of infectious vaccinia virus recombinants expressing foreign genes. J. Virol. 49:857–864.
22. Mackett, M., Smith, G., and B. Moss. 1985. The construction and characterization of vaccinia virus recombinants expressing foreign genes, p. 191–211. In D. Rickwood and B. D. Hames (ed.), DNA cloning, vol. 2. IRL Press, Washington D.C.
23. Fuerst, T., Niles, E., Studier, F., and B. Moss. 1986. Eukaryotic transient-expression system based on recombinant vaccinia virus that synthesizes bacteriophage T7 RNA polymerase. Proc. Natl. Acad. Sci. USA. 83:8122–8126.
24. Foung, S. and S. Perkins. 1989. Electric field-induced cell fusion and human monoclonal antibodies. J. Immunol. Methods. 116:117–122.
25. Perkins, S., Zimmermann, U. and S. Foung. 1991. Parameters to enhance hybridoma formation with hypo-osmolar electrofusion. Hum. Antibod. Hybridomas. 2:155–159.
26. Perkins, S. and S. Foung. 1995. Stabilizing antibody secretino of human Epstein-Barr virus activated B. lymphocytes with hybridoma formatino by electrofusion. In Nickoloff, J. (ed.), Protocols for electroporation and electrofusion of plant and animal cells, in press. Humana Press, New Jersey.
27. Hayden, D. B., Baker, N. R., Percival, M. P., and P. B. Beckwith. 1986. Modification of the Photosystem II light-harvesting chlorophyll a/b protein complex in maize during chill-induced photoinhibition. Biochim. Biophys. Acta. 851:86–92.
28. Palker, T., Tanner, M., Scearce, R., Streilein, R., Clark, M. and B. Haynes. 1989. Mapping of immunogenic regions of human T-cell leukemia type I (HTLV-I) gp46 and gp21 envelope glycoproteins with env-encoded synthetic peptides and a monoclonal antibody to gp46. J. Immunol. 142:971–978.
29. Giri, A., Markham, P., Digilio, L., Hurteau, G., Gallo, R., and G. Franchini. 1994. Isolation of a novel simian T-cell lymphotropic virus from Pan paniscus that is distantly related to the human T-cell leukemia/lymphotropic virus types I and I. J. Virol 66:8392–8395.
30. Matsushita, S., Robert-Guroff, M., Trepel, J., cossman, J., Mitsuya, H., and S. Broder. 1986. Human monoclonal antibody directed against an envelope glycoprotein of human T-cell leukemia virus type I. Proc. Natl. Acad. Sci. USA. 83:2672–2676.
31. Hayden, D. B., Baker, N. R., Percival, M. P., and P. B. Beckwith. 1986. Modification of the Photosystem II light-harvesting chlorophyll a/b protein complex in maize during chill-induced photoinhibition. Biochim. Biophys. Acta. 851:86–92.
32. Trimble, R. and G. Maley. 1984. Optimizing hydrolysis of N-linked high-mannose oligosaccharides by endo-beta-N-acetyl-glucosaminidase H. Analyt. Biochem. 141:515–522.
33. Plummer, T., Jr., Elder, J., Alexander S., Phelan, A., and A. Tarentino. 1984. Demonstration of peptide: N-glycosidase F activity in endo-beta-N-acetylglucoaminidase F preparations. J. Biol. Chem. 259:10700–10704.
34. Rowe, J., Perkins, S., Bradshaw, P., Song, G-Y, S. Fuong. 1994. Neutralizing HTLV-human monoclonal antibodies (HMAbs) to conformational epitopes. AIDS Res. Hum. Retroviruses. 10:509.
35. Lee, T., Coligan, J., Homma, T., McLane, M., Tachibana, N., and M. Essex. 1984. Human T-cell leukemia virus-associated membrane antigens: identity of the major antigens recognized after virus infection. Proc. Natl. Acad. Sci. USA. 81:3856–3860.
36. Geyer, H., Holschbach, D., Hunsmann, G., and J. Schneider. 1988. Carbohydrates of human immunodeficiency virus: structures of oligosaccharides linked to the envelope glycoproteins 120. J. Biol. Chem. 263:11760–11767.

37. Goubau, P., Liu, H., DeLange, G. Vandamme, A. and J. Desmyter. 1993. HTLV-II seroprevalence in pygmies across Africa since 1970. AIDS Res. Hum. Retroviruses. 9:709–713.
38. Kornfeld, R., and S. Kornfeld. 1985. Assembly of asparagine-linked oligosaccharides. Ann. Rev. Biochem. 54:631–664.
39. Seiki, M., Hattori, S., Hirayama, Y., and M. Yoshida. Human cell leukemia dryus: Complete sequence of the provirus vaccine integrated in leukemia cell DNA. Proc. Natl. Acad. Sci. USA. 80:3618–3622.
40. Chen, Y., Lee, T., Samuel, K., Okayama, A., Tachlbana, N., Miyoshi, I., Papas, T., and M. Essex. 1989. Antibody reactivity to different regions of human T-cell leukemia virus type I gp61 in infected people. Journal of Virology. 63:4952–4957.
41. Kiyokawa, T., Yoshikura, H., Hattori, S., Seiki, M., and Yoshida, M. 1984. Envelope proteins of human T-cell leukemia virus: Expression in Escherischia coli and its application to studies of env gene functions. Proceeding of the National Academy of Science, U.S.A. 81:6202–6206.
42. Kuga, T., Hattori, S., Yoshida, M., and T. Taniguchi. 1986. Expression of human t-cell leukemia virus type I envelope protein in *Saccharmyces cerevisiae*. Gene. 44:337–340.
43. Nyunoya, H., Ogura, T., Kikuchi, M., Iwamoto, H., Yamashita, K., Maekawa, M., Takebe, Y., Miyamura, K., Yamazaki, S., and Shimotohno, K. 1990. Expression of HTLV-I envelope protein of hydrophobic amino-terminal peptide of baculovirus polyhedrin in insect cells and its application for serological assays. AIDS Research and Human Retroviruses. 6:1311–1321.
44. Samuel, K., Lautenberger, J., Jorcyk, C., Josephs, S., Wong-Staal, F., and T. Papas. 1984. Diagnostic potential for human malignancies of bacterially produced HTLV-I envelope glycoprotein. Science. 226:1094–1097.
45. Vile, R., Schulz, T., Danos, O., Collins, M., and R. Weiss. 1991. A Murine cell line producing HTLV-I pseudotype virions carrying a selectable marker gene. Virology. 180:420–424.
46. Sattentau, Q. and J. Moore. 1995. HIV-1 neutralization is determined by epitope exposure on the gp120 oligomer. J. Exp. Med. 182:185–196.
47. Stamatatos, L. and C. Cheng-Mayer. 1995. Structural modulations of the envelope gp120 glycoprotein of human immunodeficiency virus type 1 upon oligomerization and differential V3 loop epitope exposure of isolates displaying distinct tropism upon virion-soluble receptor binding. J. Virol. 69:6191–6198.
48. Seiki, M., Hattori, S., Hirayama, Y., and M. Yoshida. 1983. Human adult T-cell leukemia virus: Complete nucleotide sequence of the provirus genome integrated in leukemia cell DNA Proc. Natl. Acad. Sci. USA. 80:3618–3622.

What we claim is:

1. A method of producing monoclonal antibodies specific for an envelope protein of HTLV-I, comprising:
   (a) administering a protein to at least one mouse to produce at least one immunized mouse, said protein being selected from the group consisting of:
      i) an isolated and purified envelope protein of Human T-cell Lymphotrophic Virus Type I (HTLV-I) devoid of non-envelope proteins of HTLV-1 having substantially the same conformation as the envelope protein in native HTLV-I;
      ii) a protein mixture of at least two isolated and purified envelope proteins of HTLV-I devoid of non-envelope proteins of HTLV-I having an apparent molecular weight which is selected from about 39 kDa, about 43 kDa, about 45 kDa, about 47 kDa and about 49 kDa, as determined by sodium dodecyl sulfate polyacrylamide gel electroghoresis; and
      iii) an isolated and purified envelope protein of HTLV-I devoid of non-envelope proteins of HTLV-I which is recognized by an antibody specific for the envelope protein of Human T-cell Lymphotrophic Virus Type II;
   (b) removing B-lymphocytes from the at least one immunized mouse;
   (c) fusing the B-lymphocytes from the at least one immunized mouse with myeloma cells, thereby producing hybridomas;
   (d) cloning the hybridomas;
   (e) selecting clones which produce anti-envelope protein antibody;
   (f) culturing the anti-envelope protein antibody-producing clones; and then
   (g) isolating anti-envelope protein antibodies from the cultures.

2. A HTLV-1 envelope protein specific human monoclonal antibody which is substantially non-binding to HTLV-I envelope protein in a denatured form.

3. The monoclonal antibody of claim 2 which binds to an isolated and purified envelope protein Human T-cell Lymphotrophic Virus Type I (HTLV-I) devoid of non-envelope proteins of HTLV-1 having substantially the same conformation as the envelope protein in native HTLV-I.

4. The monoclonal antibody of claim 2 which recognizes a conformational epitope of the envelope protein of HTLV-I.

5. The monoclonal antibody of claim 2 which neutralizes HTLV-I syncytium formation.

6. The monoclonal antibody of claim 2 which is a monoclonal antibody produced by a hybridoma selected from the group consisting of WA11/1F5, WA07/2F7, WA07/1 G7, WA 11/2E2, WA07/2F7 and WA04/2B10.

7. A method of determining the presence, in a sample, of antibodies specifically reactive with an envelope protein of HTLV-1, HTLV-II or related PTLVs, comprising the steps of:
   (a) contacting the sample with an isolated and purified envelope protein to produce complexes comprising the envelope protein and any said antibodies present in the sample specifically reactive therewith, said protein being selected from the group consisting of:
      (i) an isolated and purified envelope protein of Human T-cell Lymphotrophic Virus Type I (HTLV-I) devoid of non-envelope proteins of HTLV-1 having substantially the same conformation as the envelope protein in native HTLV-I; and
      (ii) an isolated and purified envelope protein of HTLV-I devoid of non-envelope proteins of HTLV-I which is recognized by an antibody specific for the envelope protein of Human T-cell Lymphotrophic Virus Type II; and
   (b) determining production of the complexes.

8. A method of determining the presence, in a sample, of an envelope protein of HTLV-I, comprising the steps of:
   (a) immunizing a host with an envelope protein to produce antibodies specific for the envelope protein, said protein being selected from the group consisting of:
      (i) an isolated and purified envelope protein of Human T-cell Lymphotrophic Virus Type I (HTLV-I) devoid of non-envelope proteins of HTLV-1 having substantially the same conformation as the envelope protein in native HTLV-I; and (ii) an isolated and purified envelope protein of HTLV-I devoid of non-envelope Proteins of HTLV-I which is recognized by an antibody specific for the envelope protein of Human T-cell Lymphotrophic Virus Type II;

(b) contacting the sample with the antibodies to produce complexes comprising any envelope protein of HTLV-I present in the sample and said envelope protein specific antibodies; and (c) determining production of the complexes.

9. A diagnostic kit for determining the presence of antibodies in a sample specifically reactive with an envelope protein of HTLV-1, HTLV-II or related PTLVs, comprising:

(a) an envelope protein selected from the group consisting of:

(i) an isolated and purified envelope protein of Human T-cell Lymphotrophic Virus Type I (HTLV-I) devoid of non-envelope proteins of HTLV-1 having substantially the same conformation as the envelope protein in native HTLV-1; and (ii) an isolated and purified envelope protein of HTLV-I devoid of non-envelope proteins of HTLV-I which is recognized by an antibody specific for the envelope protein of Human T-cell Lymphotrophic Virus Type II;

(b) means for contacting the envelope protein with the sample to produce complexes comprising the envelope protein and any said antibodies present in the sample; and (c) means for determining production of the complexes.

10. A diagnostic kit for detecting the presence, in a sample, of an envelope protein of HTLV-I, comprising:

(a) an antibody specifically reactive with an envelope protein selected from the group consisting of:

(i) an isolated and purified envelope protein of Human T-cell Lymphotrophic Virus Type I (HTLV-I) devoid of non-envelope proteins of HTLV-1 having substantially the same conformation as the envelope protein in native HTLV-I; and (ii) an isolated and purified envelope protein of HTLV-I devoid of non-envelope proteins of HTLV-I which is recognized by an antibody specific for the envelope protein of Human T-cell Lymphotrophic Virus Type II;

(b) means for contacting the antibody with the sample to produce a complex comprising envelope and envelope protein specific antibody; and (c) means for determining production of the complex.

* * * * *